United States Patent
Schwartz et al.

(12)

(10) Patent No.: US 6,335,360 B1
(45) Date of Patent: Jan. 1, 2002

(54) TRIPEPTIDYL PEPTIDASE INHIBITORS

(75) Inventors: Jean-Charles Schwartz, Paris; Rose Christiania, Le Mesnil St Denis, both of (FR); Froylan Vargas, Orangeburg, NY (US); Charon Robin Ganellin, Herts (GB); Lihua Zhao, Lanarkshire (GB); Samad Sanjeeda; Yondjun Chen, both of London (GB)

(73) Assignees: Institut National de la Sante et de la Recherche Medicale (INSERM); Bioprojet, both of Paris (FR)

( * ) Notice: Subject to any disclaimer, the term of this patent is extended or adjusted under 35 U.S.C. 154(b) by 0 days.

(21) Appl. No.: 09/581,830

(22) PCT Filed: Dec. 23, 1998

(86) PCT No.: PCT/EP98/08558

§ 371 Date: Sep. 18, 2000

§ 102(e) Date: Sep. 18, 2000

(87) PCT Pub. No.: WO99/33801

PCT Pub. Date: Jul. 8, 1999

(30) Foreign Application Priority Data

Dec. 23, 1997 (EP) .................................................. 97403148

(51) Int. Cl.$^7$ ..................... A61K 31/4045; C07D 209/12
(52) U.S. Cl. ............................................. 514/419; 548/492
(58) Field of Search .............................. 548/492; 514/419

(56) References Cited

FOREIGN PATENT DOCUMENTS

WO       WO 96/35805        * 11/1996

* cited by examiner

*Primary Examiner*—Deborah C. Lambkin
*Assistant Examiner*—Andrea D'Souza Small
(74) *Attorney, Agent, or Firm*—Larson & Taylor PLC

(57) ABSTRACT

The invention is relative to a compound of formula (I) and its use as an inhibitor of the CCK-inactivating peptidase tripeptidyl peptidase (TPP II). The invention concerns in particular the treatment of eating disorder, obesity, psychotic syndrome and associated psychiatric disorders. It concerns also the cosmetic use of a compound (I) in particular to aid slimming.

36 Claims, No Drawings

TRIPEPTIDYL PEPTIDASE INHIBITORS

This applicaton is a 371 of PCT/EP98/08558 filed Dec. 23, 1998.

The present invention relates to inhibitors of a membrane tripeptidyl peptidase responsible for the inactivation of endogenous neuropeptides such as cholecystokinins (CCKs).

Cholecystokinins (CCKs) are a family of hormonal and neuronal peptides which exert pleiotropic biological effects in the gut and brain. For example, CCK-33, the sulphated tritriaconta-peptide is implicated in the control of gall-bladder contraction, gastric emptying and intestinal motility (Dockray, G. J., Gastrointestinal Endocrinology: Receptors and Post-receptors Mechanisms (ed. Thompson, J.) 321–332 (Academic, New York 1990)).

In cerebral neurons, CCK immunoreactivity corresponds mainly to the sulphated carboxy-terminal octapeptide CCK-8 (Vanderhaegen, J. J., Signeau, J. C. and Gepts, W., Nature, 257, 604–605, (1975); Dockray, G. J., Nature 264, 568–570 (1976)). CCK immunoreactivity and dopamine coexist in mesolimbic neurons and may be implicated in psychotic disorders, (Hökfelt, T. et al., Nature, 285, 476–479 (1980)).

The actions of CCK are mediated by $CCK_A$ and $CCK_B$ receptors. CCK is known to have a physiological role in the control of food intake, which is enhanced by $CCK_A$ agonists (Smith, G. P. and Gibbs, J., Ann. N.Y. Acad. Sci., 713, 236–241 (1994)), and the control of anxiety, which is decreased by $CCK_B$ antagonists (Woodruff, G. and Hughes, J. A., Rev. Pharmac., 31, 469–501 (1991)).

Tripeptidyl peptidase II (TPP II) is a CCK inactivating peptidase. TPP II is found in neurons responding to cholecystokinin as well as in non-neuronal cells. TPP II is considered to be a neuropeptidase responsible for CCK-8 inactivation (Rose, C et al, Nature, 380, 403409, (1996)). TPP II has the following characteristics:
1) in two steps, it rapidly cleaves the neuropeptide CCK-8 into biologically inactive fragments with a reasonably high degree of specificity;
2) it is expressed by CCK-responsive neurons; and
3) its inhibition allows neuronal CCK-8 to escape inactivation and results in CCK-like effects such as satiation in rodents.

TPP II could be involved in CCK-8 inactivation in the gastrointestinal tract. Exogenous CCK reduces food intake and elicits other behavioural concomitants of satiation. Food intake is increased by systemic administration of $CCK_A$ receptor agonists (Smith, G. P. and Gibb, J., Ann. N.Y. Acad. Sci., 713, 236–241, (1994)). Endogenous CCK-controlling food intake seems to be of neuronal rather than hormonal origin and acts upon peripheral $CCK_A$ receptors on vagal afferent fibres (Smith, G. P. et al., Am. J. Physiol., 249, R638–R641 (1985)). In addition TPPII, although displaying preference for CCK, is also able to hydrolyse several other peptides with a free N-terminal ammonium group.

Inhibitors of TPP II are useful tools in investigating the functions of CCK neurons and may be useful drugs for the treatment of disorders such as over-eating, problems with gastrointestinal motility and psychotic syndromes.

The present invention relates to compounds which are useful in inhibiting TPP II, processes for producing these compounds, pharmaceutical compositions comprising these compounds and the use of the compounds to inhibit TPP II.

The present invention provides a compound of the following formula I:

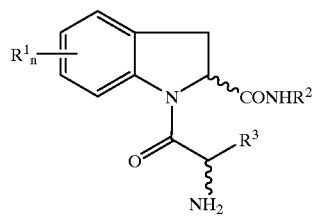

(I)

wherein: each $R^1$ may be the same or different, and is chosen from
halogen; OH; $C_1$–$C_6$ alkyl, $C_1$–$C_6$ alkenyl or $C_1$–$C_6$ alkynyl, optionally substituted by at least one halogen, OH or mixtures thereof; X($C_1$–$C_6$ alkyl), wherein X is S, O or OCO, and the alkyl is optionally substituted by at least one halogen, OH or mixtures thereof; $SO_2$($C_1$–$C_6$ alkyl), optionally substituted by at least one halogen; or $YSO_3H$, $YSO_2$($C_1$–$C_6$ alkyl), wherein Y is O or NH and the alkyl is optionally substituted by at least one halogen; a diradical —$X^1$—($C_1$–$C_2$ alkylene)—$X^1$— wherein $X^1$ is O or S; a benzene ring fused to the indoline ring;
n is from 0 to 4;
$R^2$ is $CH_2R^4$, wherein $R^4$ is
$C_1$–$C_6$ alkyl substituted by at least one halogen, OH or mixtures thereof; $(CH_2)_pZ(CH_2)_qCH_3$, wherein Z is O or S, p is from 0 to 5 and q is from 0 to 5, provided that p+q is from 0 to 5;
$C_2$–$C_6$ unsaturated alkyl; or $C_3$–$C_6$ cycloalkyl; or $R^2$ is $C_1$–$C_6$ alkyl or O($C_1$–$C_6$ alkyl), each optionally substituted by at least one halogen;
$R^3$ is H; $C_1$–$C_6$ alkyl optionally substituted by at least one halogen; $(CH_2)_pZR^5$ wherein p is from 1 to 3, Z is O or S and $R^5$ is H or $C_1$–$C_3$ alkyl; benzyl;
or a pharmaceutically acceptable acid addition salt thereof;

The invention provides in particular a compound of the above formula I wherein: each $R^1$ may be the same or different, and is chosen from
halogen; OH; $C_1$–$C_6$ alkyl, optionally substituted by at least one halogen, OH or mixtures thereof; X($C_1$–$C_6$ alkyl), wherein X is S, O or OCO, optionally substituted by at least one halogen, OH or mixtures thereof; $SO_2$($C_1$–$C_6$ alkyl), optionally substituted by at least one halogen; or $YSO_3H$, $YSO_2$($C_1$–$C_6$ alkyl), wherein Y is O or NH optionally substituted by at least one halogen;
n is from 0 to 4;
$R^2$ is $CH_2R^4$, wherein $R^4$ is
$C_1$–$C_6$ alkyl substituted by at least one halogen, OH or mixtures thereof; $(CH_2)_pZ(CH_2)_qCH_3$, wherein Z is O, S, p is from 0 to 5 and q is from 0 to 5, provided that p+q is from 0 to 5; $C_2$–$C_6$ unsaturated alkyl; or $C_3$–$C_6$ cycloalkyl,
or $R^2$ is $C_1$–$C_6$ alkyl or O($C_1$–$C_6$ alkyl), each optionally substituted by at least one halogen;
$R^3$ is H or $C_1$–$C_6$ alkyl;
or a pharmaceutically acceptable acid addition salt thereof.

Compounds of formula (I) wherein n=0 or when n is not 0 wherein $R^1$ is a halogen atom, a O($C_1$–$C_4$)alkyl, OH or a ($C_1$–$C_4$)alkyl group, $R^2$ is $CH_2R^4$ with $R^4$ being $(CH_2)_2SCH_3$, $(CH_2)_2OH$ or cyclohexyl or $R^2$ is a ($C_1$–$C_6$) alkyl group, and $R^3$ is an hydrogen atom or a ($C_1$–$C_4$)alkyl group, are known from WO 96/35805 and are not included in the present invention.

According to one aspect of the present invention, it is relative to compounds of formula (I) wherein $R^2$ is $CH_2R^4$, $R^4$ being $C_1$–$C_6$ alkyl substituted by at least one halogen; $(CH_2)_pZ(CH_2)_qCH_3$ wherein Z is O (p and q are as defined above); $C_2$–$C_6$ unsaturated alkyl; or $R^2$ is O($C_1$–$C_6$)alkyl optionally substituted by at least one halogen.

According to another aspect of the present invention, it is relative to compounds of formula (I) wherein n is not 0 and $R^1$ is $C_1$–$C_6$ alkyl substituted by at least one halogen, OH or mixtures thereof; X($C_1$–$C_6$ alkyl) wherein X is S or OCO, optionally substituted by at least one halogen, OH or mixtures thereof; O($C_1$–$C_6$)alkyl substituted by at least one halogen, OH or mixtures thereof; $SO_2$($C_1$–$C_6$ alkyl), optionally substituted by at least one halogen; or $YSO_3H$, $YSO_2$($C_1$–$C_6$ alkyl) wherein Y is O or NH optionally substituted by at least one halogen.

According to another aspect, the present invention is directed to compounds (I) wherein n is not 0 and $R^1$ represents a $C_1$–$C_6$ alkenyl or $C_1$–$C_6$ alkynyl group.

The alkyl groups may be straight-chain or branched. The alkyl groups have from 1 to 6 carbon atoms, preferably from 1 to 4 carbon atoms. Suitable alkyl groups include methyl, ethyl, n-propyl, i-propyl, n-butyl, i-butyl or t-butyl. Preferred alkyl groups are $C_{1-4}$ straight chain alkyl. Typically a substituted alkyl group has from 1 to 6 substituents and preferably from 1 to 3 substituents. Halogen is typically F,Cl,Br, or I, preferably Cl or F, most preferably F.

The alkenyl or alkynyl groups may be straight-chain or branched. These groups contain from 1 to 6 carbon atoms, preferably from 1 to 4 carbon atoms.

Typical alkenyl groups include ethenyl.

Typical alkynyl groups include ethynyl.

Unsaturated alkyl groups (in $R^2$) contain one or more double or triple bonds.

According to still another aspect of the invention, it is relative to compounds (I) wherein $R^1$ is a diradical —$X^1$—($C_1$–$C_2$ alkylene)—$X^1$— where $X^1$ is as defined above. $R^1$ is typically —$OCH_2O$—.

The diradical is preferably attached to the indoline ring at the positions 4 and 5 (4,5-positions) or at the positions 5 and 6 (5,6-positions).

According to another aspect, the invention is directed to compounds (I) wherein $R^1$ represents a benzene ring fused to the indoline ring.

The benzene ring is preferably attached at the 4-positions, or at the 5,6-positions.

The present invention provides also compounds (I) wherein $R^3$ represents a $C_1$–$C_6$ alkyl substituted by at least one halogen; $(CH_2)_pZR^5$ where p, Z and $R^5$ are as defined above, or a benzyl.

Preferably $R^3$ is hydrogen, methyl or ethyl, and most preferably $R^3$ is ethyl.

Preferably $R^2$ is $CH_2R^4$, wherein $R^4$ is $CF_3$, $CF_2CF_3$, $CH_2OCH_3$, $CH_2SCH_3$, $SCH_3$, $CH(OH)CH_3$, $CH_2F$, $CH_2Cl$, C=$CH_2$, C=CH, or cyclopropyl, or $R^2$ is $NHCH_3$. More preferably $R^4$ is $CH_2OCH_3$, $CH(OH)CH_3$, $CH_2SCH_3$, or $R^4$ contains one or more halogen substituents, preferably the or each halogen is fluorine or chlorine, for example $CH_2Cl$, $CH_2F$, $CHF_2$, $CF_3$ or $CF_2CF_3$, and most preferably $R^4$ is $CF_3$.

Each $R^1$, which may be the same or different is preferably, $CH_3$, $OCH_3$, Cl, F, OH, $OCF_3$, $OSO_3H$, $OSO_2CH_3$, $OCOCH_3$, $OSO_2CF_3$, $SO_2CH_3$, $SCH_3$, $NHSO_2CH_3$ or $CF_3$. Most preferably each $R^1$ is $OCH_3$, OH, Cl or F.

The number of substituents $R^1$ is 0, 1, 2, 3 or 4, and preferably, n is 0, 1 or 2. When n is 1, $R^1$ is preferably at the 4-, 5- or 6-position, most preferably at the 4- or 5-position. When n is 2, the two $R^1$ groups are preferably at the 4- and 5-positions, 4- and 6-positions or 5- and 6-positions, and are most preferably at the 4- and 5-positions. When n is 3, the three $R^1$ groups are preferably at the 4-, 5- and 6-positions.

The compounds of the invention generally have at least two chiral centres. These are the carbon atoms at the 2-position on the indoline ring and the carbon atom to which $R^3$ is attached. The stereochemistry at each of the chiral centres may independently be (S) or (R). Preferably the stereochemistry of at least one chiral centre is (S). Most preferably the stereochemistry at both chiral centres is (S). The (S),(S) stereochemistry corresponds to the stereochemistry of naturally occurring amino acids. However, it is not essential that the stereoisomers are separated. For example 1-(2(S)-aminobutyryl)4-chloroindoline-2(R/S)-carboxylic acid (2,2,2-trifluoroethyl)amide trifluoroacetate and 1-(2(S)-aminobutyryl)4-fluoroindoline-2(R/S)-carboxylic acid (2,2,2-trifluoroethyl)amide trifluoroacetate have been shown to have useful activity.

The invention also provides a method for inhibiting the activity of TPP II which comprises administering an effective amount of a compound of formula I or a pharmaceutically acceptable acid addition salt thereof to a mammalian subject.

In this respect, the invention provides a medicament acting as an inhibitor of the CCK-inactivating peptidase tripeptidyl peptidase (TPPII) and/or for the treatment of eating disorders, especially obesity and/or for the treatment of psychotic syndromes and associated psychiatric disorders, which comprises a therapeutically effective amount of a compound of formula I.

The invention also provides a compound of formula I or pharmaceutical compositions comprising a compound of formula I for use in the treatment of the human or animal body, particularly for the treatment of eating disorders, especially obesity.

The invention further provides the use of a compound of formula I for the manufacture of a medicament for inhibiting the activity of TPP II and/or for treating eating disorders, especially obesity.

The compounds of the invention may be administered alone or together with any other known compound for the treatment for obesity. Suitable treatments include those known in the art, for example treatment with an adrenergic $β_3$-receptor agonist, a histamine $H_3$-receptor antagonist, a neuropeptide Y receptor (NPY-5)antagonist, a compound acting on the amylin receptor or a compound that increases the levels of noradrenaline, dopamine or serotonin in the brain e.g. dexfenfluramine, sibutramine or fluoxetine. The compound of formula I and the other obesity treatment compound may be provided in a form for simultaneous, separate or sequential administration.

The invention also provides a compounds of formula I or a pharmaceutical composition comprising a compound of formula I for the treatment of psychotic syndromes and associated psychiatric disorders.

The invention also provides the cosmetic use of compound of formula I to aid slimming.

In this respect, the invention provides a cosmetic composition comprising a compound of formula I together with a physiologically acceptable carrier or diluent.

It is provided also a non-therapeutic method of treatment of the human body for slimming, comprising administering an effective amount of a compound of formula I optionally with a physiologically acceptable carrier or diluent.

The compounds of formula I may be prepared by the following general procedure:

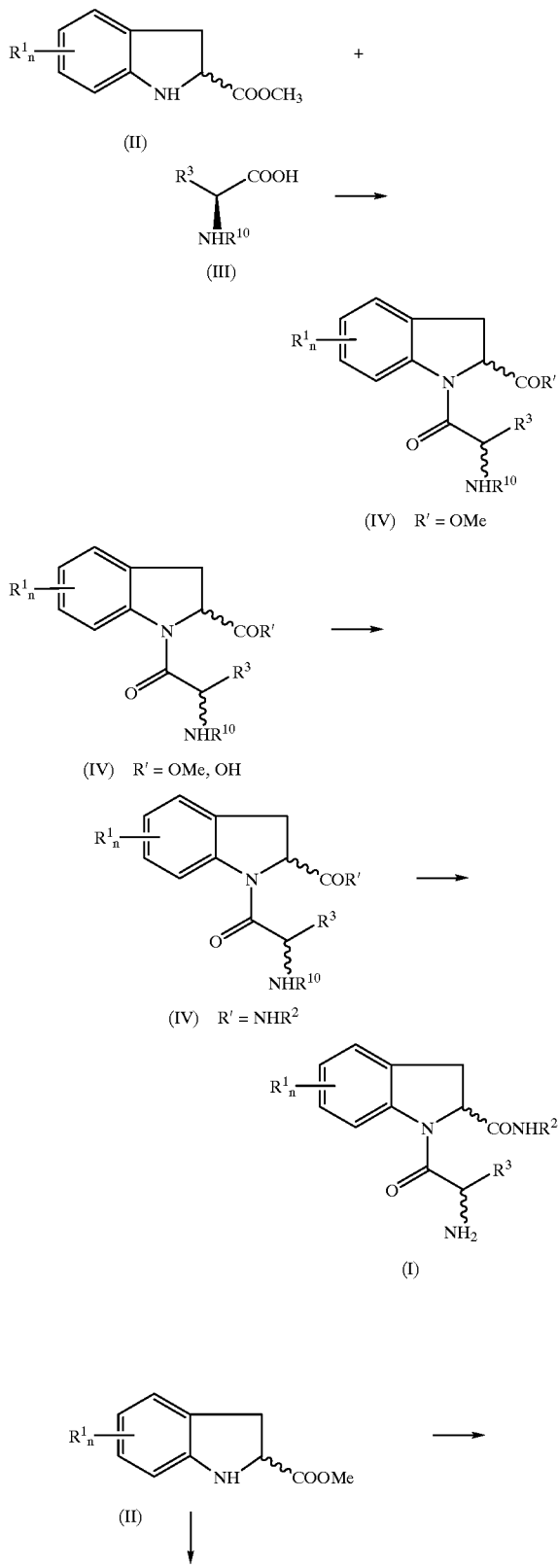

$R^1$, $R^2$, $R^3$ are as defined above and $R^{10}$ is H or a protecting group (e.g. benzyloxycarbonyl or t-butyloxycarbonyl).

a. Indole (or appropriately substituted indole)-2-carboxylic acid alkyl ester is reduced to the indoline ester (II) by magnesium turnings in methanol, and this is coupled with a suitably protected amino acid (III) in the presence of a coupling reagent, such as bis(2-oxo-3-oxazolidinyl) phosphinic chloride (BOPCl) or a carbodiimide such as diisopropylcarbodiimide (DIC), dicyclohexylcarbodiimide (DCC) or 1-(3-dimethylaminopropyl)-3-ethylcarbodiimide methiodide to form IV, where $R^1$ is OMe.

b. The acid of formula IV, where $R^1$ is OH, may then be prepared by hydrolyzing the corresponding ester of formula IV wherein $R^1$ is OMe with sodium hydroxide or lithium hydroxide in methanol-water solution at room temperature.

C. The diamides of formula IV, wherein $R^1$ is $NHR^2$, are formed by coupling the acid of formula IV, where $R^1$ is OH, with an amine, $R^2NH_2$, or a salt thereof in the presence of a coupling reagent, such as BOPCl, DIC, DCC etc.; or by reacting the ester of formula IV wherein $R^1$ is OMe with excess amine, e.g. $MeOCH_2CH_2NH_2$, $MeSCH_2CH_2NH_2$, $MeCH(OH)CH_2NH_2$ etc., at a temperature between 15 and 60° C.

d. Removal of the protecting group $R^{10}$ from the compound of formula IV where $R^1$ is $NHR^2$ to give compound I can be effected by hydrogenation when $R^{10}$ is benzyloxycarbonyl over a catalyst such as palladium on activated carbon; or by trifluoroacetic acid when $R^{10}$ is tert-butoxycarbonyl in dichloromethane.

e. An alternative route to obtain the diamides of formula IV wherein $R^1$ is $NHR^2$, is to prepare an indoline 2-substituted carboxamide of formula V, then couple it with the amino acid of formula III to obtain a compound of formula IV wherein $R^1$ is $NHR^2$. Removal of the protecting group $R^{10}$ can be effected as described above. The compound of formula V can be prepared by reacting the indoline ester II with excess amine with or without methanol (when the amine is reactive), at a temperature between 15 and 60° C., or by hydrolyzing the protected indoline ester to its acid, then treating the acid with an amine in the presence of a coupling reagent (such as BOPCl, DIC or DCC), followed by the removal of the protecting group, $R^{10}$ as described above.

wherein $R^1$, $R^2$, $R^3$ and $R^{10}$ are as defined above.

The products obtained by these procedures can be converted into a salt.

Physiologically acceptable salts according to the invention which may be conveniently used include physiologically acceptable acid addition salts, including the hydrochloride, acetate, trifluoroacetate and oxalate.

Acid addition salts according to the invention include mono- and di-carboxylic acids in which the non-carbonyl moiety of the carboxylate grouping is selected from straight or branched chain alkyl (e.g. methyl, n-propyl, n-butyl or t-butyl); cyclic alkyl (e.g. cyclohexyl); alkoxyalkyl (e.g. methoxymethyl), carboxyalkyl (e.g. carboxyethyl), aralkyl (e.g. benzyl), aryloxyalkyl (e.g. phenoxymethyl), aryl (e.g. phenyl optionally substituted by halogen, $C_{1-4}$ alkyl or $C_{1-4}$ alkoxy or amino); sulfonic acids such as alkyl- or aralkyl-sulfonate (e.g. methanesulfonate); mono- or di-phosphoric acids which may or may not be blocked, amino acids (e.g. L-valine or L-isoleucine) and nitrate. With regards to these acid components, unless otherwise specified, any alkyl moieties present in such acids preferably contain from 1 to 18 carbon atoms, particularly from 1 to 4 carbon atoms, in the case of straight chain alkyl groups, or 3 to 7 carbon atoms in the case of branched or cyclic alkyl groups. Any aryl moiety present in such acids advantageously comprises a phenyl group.

Any reference herein to any of the above compounds of the invention also includes a reference to the physiologically acceptable salts thereof.

Particular compounds of formula I include:

1-(2(S)-aminobutyryl)-5-chloroindoline-2(S)-carboxylic acid (2,2,2-trifluoroethyl)amide;

1-(2(S)-aminobutyryl)-5-chloroindoline-2(S)-carboxylic acid 2-chloroethylamide;

1-(2(S)-aminobutyryl)-indoline-2(S)-carboxylic acid (2-methylthioethyl)amide;

1-(2(S)-aminobutyryl)-indoline-2(S)-carboxylic acid N-(cyciopropylmethyl)amide;

1-(2(S)-aminobutyryl)-indoline-2(S)-carboxylic acid (2,2,2-trifluoroethyl)amide;

1-(2(S)-aminobutyryl)-5-hydroxyindoline-2(R/S)-carboxylic acid (2,2,2,-trifluoroethyl)amide;

1-(2(S)-aminobutyryl)4-chloroindoline-2(R/S)-carboxylic acid (2,2,2-trifluoroethyl)amide;

1-(2(S)-aminobutyryl)4-fluoroindoline-2(R/S)-carboxylic acid (2,2,2-trifluoroethyl)amide;

1-(2(S)-aminobutyryl)-5-methoxyindoline-2(R/S)-carboxylic acid (2,2,2-trifluoroethyl)amide;

1-(2(S)-aminobutyryl)-5-trifluoromethoxyindoline-2(R/S)-carboxylic acid (2,2,2-trifluoroethyl)amide;

and pharmaceutically acceptable salts thereof.

Particular compounds of formula I include also:

1-[2-(S)-aminobutyryl]-4,5-dichloro-indoline-2-(R/S)-carboxylic acid butyl amide 1-[2-(S)-aminobutyryl]-4,5-dichloro-indoline-2-(S)-carboxylic acid 2,2,2-trifluoroethylamide 1-[2-(S)-aminobutyryl]-5,6-dichloro-indoline-2-(S)-carboxylic acid 2,2,2-trifluoroethylamide 1-[2-(S)-aminobutyryl]-benz-[e]-indoline-2-(S)-carboxylic acid 2,2,2-trifluoroethylamide 1-[2-(S)-aminobutyryl]-5-O-sulfato-indoline-2(R/S)-carboxylic acid butyl amide 1-[2-(S)-aminobutyryl]-benz-[e]-indoline-2-(S)-carboxylic acid butyl amide 1-[2-(S)-aminobutyryl]-4,5-dichloro-indoline-2-(R/S)-carboxylic acid 2,2,2-trifluoroethylamide 1-[2-(S)-aminobutyryl]-5-O-sulfato-indoline-2(R/S)-carboxylic acid trifluoroethylamide 1-[2-(S)-aminobutyryl]-benz[f]-indoline-2-(S/R)-carboxylic acid 2,2,2-trifluoroethylamide 1-[2-(S)-phenylalanyl)-5-Chloro-indoline-2(R/S)-carboxylic acid 2,2,2-trifluoroethylamide 1-[2(S)-aminobutyryl]-4-methoxyindoline-2(S)-carboxylic acid (2,2,2-trifluoroethyl)amide 1-[2-glycyl]-5-chloroindoline-2(R/S)-carboxylic acid (2,2,2-trifluoroethyl)amide 1-[2(S)-alanyl]-5-chloroindoline-2(R/S)-carboxylic acid (2,2,2-trifluoroethylamide 1-[2(S)-norvalyl]-5-chloroindoline-2(R/S)-carboxylic acid (2,2,2-trifluoroethyl)amide 5 1-[2(S)-methionyl]-5-chloroindoline-2(R/S)-carboxylic acid (2,2,2-trifluoroethyl)amide 1-[2(S)-aminobutyryl]-4-methylindoline-2(R/S)-carboxylic acid (2,2,2-trifluoroethyl)amide 1-[2(S)-aminobutyryl]-4,5-dimethoxyindoline-2(R/S)-carboxylic acid (2,2,2-trifluoroethyl)amide 1-[2(S)-aminobutyryl]-4,5-methylenedioxyindoline-2(R/S)-carboxylic acid (2,2,2-trifluoroethyl)amide 1-[2(S)-aminobutyryl]-5-ethynylindoline-2(R/S)-carboxylic acid (2,2,2-trifluoroethyl)amide and pharmaceutically acceptable salts thereof.

In addition to the above, compounds of formula I which, in vitro, have a Ki value of less than 1.0 nM are especially preferred.

The compounds of formula I may be used in vitro or in vivo as TPP II inhibitors. For in vivo use, the compounds may be useful in the development and standardisation of assays for TPP II and inhibitors thereof.

For in vivo use the compounds may be useful in the control of stomach emptying and control of appetite for food.

The compounds of formula I may be administered to mammals including humans, by any route appropriate to the condition to be treated. Suitable routes include oral, rectal, nasal, topical (including buccal and sublingual), vaginal and parenteral (including subcutaneous, intramuscular, intravenous, intradermal, intrathecal and epidural). It will be appreciated that the preferred route may vary with, for example, the condition of the recipient.

For each of the above-identified utilities and indications, the amount required of the individual active ingredients will depend upon a number of factors including the severity of the condition to be treated and the identity of the recipient, and will also be at the discretion of the attendant physician. In general, however, for each of these utilities and indications, a suitable, effective dose will be in the range of from 0.001 to 10 mg per kilogram body weight per day and most preferably in the range of from 0.01 to 1 mg per kilogram body weight per day. Unless otherwise indicated, all weights of active ingredient are calculated as the parent compound, and for salts thereof the figures would be increased proportionately.

The desired dose may suitably be presented as two, three, four or more sub-doses administered at appropriate intervals throughout the day. These sub-doses may be administered in unit dosage forms, for example containing from 0.01 to 1000 mg, preferably from 0.01 to 500 mg of active ingredient per unit dosage form.

Doses of compounds of the invention may be administered at sub-daily or daily intervals, or less frequently, for example on alternate days, weekly or fortnightly. In general the doses will be the same as the above daily dose, although higher doses, particularly when formulated to be released over a prolonged period of time, may be used.

While it is possible for the compounds to be administered alone it is preferable to present them as pharmaceutical formulations. The formulations of the present invention comprise at least one active ingredient, as above defined, together with one or more acceptable carriers thereof and optionally other therapeutic ingredients. The carrier(s) must be "acceptable" in the sense of being compatible with the other ingredients of the formulation and not deleterious to the recipients thereof.

The formulations include those suitable for oral, rectal, nasal, topical (including buccal and sublingual), vaginal or parenteral (including subcutaneous, intramuscular, intravenous, intradermal, intrathecal and epidural) administration. The formulations may conveniently be presented in unit dosage form and may be prepared by any of the methods well known in the art of pharmacy. Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

Formulations of the present invention suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion.

A tablet may be made by compression or moulding, optionally with one or more accessory ingredients. Compressed tablets may be prepared by compressing in a suitable machine the active ingredient in a free-flowing form such as a powder or granules, optionally mixed with a binder (e.g. povidone, gelatin, hydroxypropylmethyl cellulose), lubricant, inert diluent, preservative, disintegrant (e.g. sodium starch glycolate, cross-linked povidone, cross-linked sodium carboxymethyl cellulose), surface-active or dispersing agent.

A capsule may be made by filling a loose or compressed powder on an appropriate filling machine, optionally with one or more additives. Examples of suitable additives include binders such as povidone; gelatin, lubricants, inert diluents and disintegrants as for tablets.

Compositions suitable for transdermal administration may be presented as discrete patches adapted to remain in intimate contact with the epidermis of the recipient for a prolonged period of time. Such patches suitably contain the active compound 1) in an optionally buffered, aqueous solution or 2) dissolved in an adhesive or 3) dispersed in a polymer. A suitable concentration of the active compound is about 1% to 35%, preferably about 3% to 15%.

Formulations suitable for parenteral administration include aqueous and non-aqueous sterile injection solutions which may contain antioxidants, buffers, bacteriostats and solutes which render the formulation isotonic with the blood of the intended recipient; and aqueous and non-aqueous sterile suspensions which may include suspending agents and thickening agents, and liposomes or other microparticulate systems which are designed to target the compound to blood components or one or more organs. The formulations may be presented in unit-dose or multi-dose containers, for example sealed ampoules and vials, and may be stored in a freeze-dried (lyophilized) condition requiring only the addition of the sterile liquid carrier, for example water for injections, immediately prior to use.

The following Examples illustrate the invention.

The following abbreviations are used hereafter:

Abu: aminobutyryl; Ar: aromatic; Bn: benzyl; Boc: t-butoxycarbonyl; Ph: phenyl; t-Bu: t-butyl; s: singlet; d: doublet; t: triplet; m: multiplet; dd: double doublet; w: weak; vs: very small; str: strong.

EXAMPLE 1

Synthesis of 1-(2(S)-aminobutyryl)-5-chloroindoline-2(S)-carboxylic acid (2,2,2-trifluoroethyl)amide trifluoroacetate 5-Chloroindoline-2(R/S)-carboxylic acid methyl ester 5-Chloroindoline2-carboxylic acid ethyl ester (3 g, 13.4 mmol) and magnesium turnings (0.652 g, 26.8 mmol) were suspended in dried methanol (300 ml). This mixture was stirred at 5 to 10° C. under nitrogen for 3 hours, then poured into dichloromethane (400 ml), and washed with saturated ammonium chloride solution, the organic layer was separated, and the aqueous layer was extracted with dichloromethane (3×100 ml). The combined organic layers were dried over sodium sulphate and evaporated. The resulting solid was chromatographed on silica gel using dichloromethane as eluent, to furnish the indoline ester as a yellow solid.

MS (EI) m/z 211 (M$^+$, 100), 152 (M, 81). $^1$HNMR (CDCl$_3$, 400 MHz) δ (ppm) 6.70–7.05(m, 2H, ArH), 6.63 (d, 1H, ArH), 4.25–4.45 (m, 2H, NH and NCHCO of indoline), 3.77 (s, 3H, OCH$_3$), 3.29–3.42 (m, 2H, CH$_2$ of indoline).

1-(N-t-Butoxycarbonyl-2(S)-aminobutyryl)-5-chloroindoline-2(S)-carboxylic acid methyl ester To a solution of 5-chloroindoline-2(R/S)-carboxylic acid methyl ester (1.2 g, 5.69 mmol) and N-t-butoxycarbonyl-2(S)-aminobutyric acid (1.27 g, 6.25 mmol) dissolved in dried dichloromethane (10 ml) under nitrogen at 10° C., was added diisopropylcarbodiimide (0.98 ml, 6.30 mmol). The mixture was stirred at room temperature for 24 hours, then filtered. The filtrate was evaporated under vacuum to afford a brown solid which was purified by column chromatography on silica gel using 20:1 dichloromethane: diethyl ether as eluent. A white foam was obtained which was the mixture of two diastereomers. The two diastereomers were separated by column chromatography on silica gel using 7:3 petroleum spirit:diethyl ether as eluent, and the pure (S,S) form was obtained as a white foam.

MS (Fab) m/z 397 (MH$^+$, 8), 211 (49), 189(66), 145(100), 102 (56), 57 (91). $^1$HNMR (CDCl$_3$, 400 MHz) δ (ppm) 8.19 (d, 1H, ArH), 7.06–7.24 (m, 2H, ArH), 5.23–5.42 (dd, 1H, NCHCO of indoline), 5.02 (d, 1H, NH of Abu), 4.86–4.95, 4.33–4.39 (m, 1H, CH of Abu), 3.68, 3.69 (2s, 3H, OCH$_3$), 3.07–3.08, 3.30–3.62 (m, 2H, CNCHCO of indoline), 1.59–2.05 (m, 2H, CH$_2$ of Abu), 1.44 (s, 9H, t-Bu), 1.09, 0.98 (2t, 3 H, CH$_3$ of Abu).

1-N-t-Butoxycarbonyl-2(S)-aminobutyryl)-6-chloroindoline-2(S)-carboxylic acid

To the solution of 1 -(N-t-butoxycarbonyl-2(S)-aminobutyryl)-5-chloroindoline-2(S)-carboxylic acid methyl ester (1.2 g, 3 mmol) in methanol (20 ml), was added sodium hydroxide(0.24 g, 6 mmol) in water (10 ml). The solution was stirred at 5–10° C. for 4 hours. The mixture was poured into dichloromethane (50 ml), and washed with cold potassium hydrogen sulphate (3×20 ml), then water (30 ml). The organic layer was dried over sodium sulphate, and evaporated to provide a white foam which was pure enough for the next reaction.

MS (Fab) m/z 383(MH$^+$, 8), 327(14), 197(12),145(63), 58(100). $^1$HNMR (CDCl$_3$, 400 MHz) δ (ppm) 8.20 (d, 1H, ArH), 7.18–7.25 (m, 2H, ArH), 5.66–6.50(m, 2H, NCHCO of indoline, COOH), 5.08–5.20 (dd, 1H, NH of Abu), 4.70–4.80 (m, 1H, CH of Abu), 3.42–3.70 (m, 2H, CH$_2$ of indoline), 1.50–2.00 (m, 2H, CH$_2$ of Abu), 1.57 (s, 9H, t-Bu), 1.05 (t, 3H, CH$_3$ of Abu).

1-(N-t-Butoxycarbonyl-2(S)-aminobutyryl)-5-chloroindoline-2(S)-carboxylic acid (2,2,2-trifluoroethyl)amide 1-(N-t-Butoxycarbonyl-2(S)-aminobutyryl)-5-chloroindoline-2(S)-carboxylic acid (0.192 g, 0.5 mmol) and 2,2,2-trifluoroethylamine hydrochloride (0.205 g, 1.5 mmol) were dissolved in dried dichloromethane (5 ml) under nitrogen at 0° C., and triethylamine (0.63 ml, 4.5 mmol) was added followed by bis(2-oxo-3-oxazolidinyl)phosphinic chloride (0.382 g, 1.5 mmol). The temperature was allowed to rise to room temperature and the mixture was stirred at room temperature for 24 hours, then filtered. The filtrate was concentrated under vacuum to give a brown solid which was columned on silica gel using 7:3 petroleum spirit: ethyl acetate as eluent to provide a white solid.

MS (Fab) m/z 464(MH$^+$, 4), 408(8), 278(14), 152(24), 58(100). $^1$HNMR (CDCl$_3$, 400 MHz) δ (ppm) 8.23–8.30 (m, 1H, CONH), 7.96–8.05(m, 1H, ArH), 7.21–7.23(m, 2H, ArH), 4.83–5.17 (m, 2H, NCHCO of indoline and NH of Abu), 3.41–4.09 (m, 5H, CH of Abu, CH$_2$ of indoline, CH$_2$CF$_3$), 0.85–1.98 (m, 14H, CH$_2$of Abu, t-Bu, CH$_3$ of Abu).

1-2(S)-Aminobutyryl)-5-chloroindoline-2(S)-carboxylic acid (2,2,2-trifluoroethyl)amide trifluoroacetate 1-(N-t-Butoxycarbonyl-2(S)-aminobutyryl)-5-chloroindoline-2(S)-carboxylic acid (2,2,2-trifluoroethyl) amide (120 mg, 0.26 mmol) was dissolved in dichloromethane (1 ml) in an ice-water bath, and trifluoroacetic acid (1 ml) was added under nitrogen. The solution was stirred at 0 to 5° C. until gas evolution ceased. The solution was evaporated to dryness in vacuo and the residue was treated with dried diethyl ether. A white foam was obtained after drying.

m.p. 34–35° C. MS (Fab) m/z 364(MH$^+$, 29), 58(100). $^1$HNMR (DMSO-d$_6$, 400 MHz) δ (ppm) 8.90–9.40, 8.85–8.92(m, 1H, CONH), 8.08–8.70, 7.10–7.50(m, 6H, acidic H, ArH), 5.10–5.35 (m, 1H, NCHCO of indoline), 2.80–4.25 (m, 5H, CH$_2$CF$_3$, CH of Abu, CH$_2$ of indoline), 1.75–2.00 (m, 2H, CH$_2$ of Abu), 0.70–1.29(m, 5H, CH$_3$ of Abu, H$_2$O overlap). IR (KBr) cm$^{-1}$ 3430(broad, w) (N—H, O—H); 1687(vs), 1676(vs), 1632(w) (C=O); 1560(w), 1478(s) (C=C); 1207(s), 1167(vs), 1126(s) (C—O, C—N, C—F). Elemental Analysis: calculated for C$_{15}$H$_{17}$ClF$_3$N$_3$O$_2$, 1.7CF$_3$COOH, C, 39.63, H, 3.38, N, 7.54%, found C, 39.45, H, 3.32, N, 7.43%.

EXAMPLE 2

Synthesis of 1-2(S)-aminobutyryl)-5-chloroindoline-2(S)-carboxylic acid 2-chloroethylamide trifluoroacetate 1-(N-t-Butoxycarbonyl-2(S)-aminobutyryl)-S-chloroindoline-2(S)-carboxylic acid 2-chloroethylamide Triethylamine (0.42 mL, 3 mmol) was added to the solution of 1-(N-t-butoxycarbonyl-2(S)-aminobutyryl)-5-chloroindoline-2(S)carboxylic acid (0.152 g, 0.4 mmol) and 2-chloroethylamine hydrochloride (0.116 g, 1 mmol) in dried dichloromethane (10 ml) under nitrogen at 0° C., followed by bis(2-oxo-3-oxazolidinyl)phosphinic chloride (0.255 g, 1.0 mmol). The temperature was allowed to rise to room temperature and the mixture was stirred at room temperature for twenty-four hours, then filtered. The filtrate was concentrated under vacuum to give a brown solid which was purified by column chromatography (silica gel, diethyl ether) to provide a white solid.

MS (FAB) m/z 445(MH$^+$, 12), 444(33), 330(52), 258(46), 152(63), 57(100). $^1$HNMR (CDCl$_3$, 400 MHz) δ (ppm) 8.0–8.1 (m, 1H, CONH), 7.68–7.8 (m, 1H, ArH), 7.18–7.25 (m, 2H, ArH), 5.02–5.10 (m, 1H, H2 of indoline), 4.80–4.90 (m, 1H, NH of Abu), 4.08–4.18 (m, 1H, CH of Abu), 3.40–3.75 (m, 6H, H3 of indoline, CH$_2$CH$_2$Cl), 1.63–1.89 (m, 2H, CH$_2$ of Abu), 1.46 (s, 9H, t-Bu), 0.95–1.23 (m, 3H, CH$_3$ of Abu).

1-(2(S)-Aminobutyryl)-5-chloroindoline-2(S)-carboxylic acid 2-chloroethylamide trifluoroacetate Trifluoroacetic acid (1 mL) was added dropwise to the solution of 1-(N-t-butoxycarbonyl-2(S)-aminobutyryl)-5-chloroindoline-2(S)-carboxylic acid 2-chloroethylamide (100 mg, 0.225 mmol) in dichloromethane (1 mL) in an ice-water bath under nitrogen. This solution was stirred at 0–5° C. until gas evolution ceased, then evaporated to dryness under vacuum below 45° C., and the residue was treated with dried diethyl ether. A pink foam was obtained after drying.

m.p. 80–88° C. MS (FAB) m/z 348(M+4, 8), 347(M+3, 8), 346(M+2, 37), 345(MH$^+$, 13), 344(M, 60), 145(33), 57(100). $^1$HNMR (DMSO-d$_6$, 400 MHz) δ (ppm) 8.70–8.92 (m, 1H, CONH), 8.20–8.50 (m, 3H, acidic H), 8.10 (d, 1H, J=8.5 Hz, ArH), 7.25–7.42 (m, 2H, ArH), 5.10 (dd, 1H, H2 of indoline), 3.10–3.76 (m, 7H, CONCH$_2$CH$_2$Cl, CH of Abu, H3 of indoline), 1.75–2.00 (m, 2H, CH$_2$ of Abu), 0.9–1.18 (m, 3H, CH$_3$ of Abu). IR (KBr disc) cm$^{-1}$ 3330 (broad, w) (N—H, O—H); 1669(vs), 1676(vs) (C=O); 1536(w), 1478(s) (C=C); 1202(s), 1140(vs) (C—O, C—N, C—F). Elemental Analysis: calculated for C$_{15}$H$_{19}$Cl$_2$N$_3$O$_2$, 1.2CF$_3$COOH: C, 43.44; H, 4.23; N, 8.73%. Found: C, 43.17; H, 4.52; N, 8.40%.

EXAMPLE 3

Synthesis of 1-(2(S)-aminobutyryl)-indoline-2(S) carboxylic acid (2-methylthioethyl)amide trifluoroacetate 1-(N-t-Butoxycarbonyl-2(S)-aminobutyryl)-indoline-2(S)-carboxylic acid-(2-methylthioethyl)amide To a solution of 1-(N-t-butoxycarbonyl-2(S)-aminobutyryl)-indoline-2(S)-carboxylic acid methyl ester (0.5 g, 1.4 mmol) in methanol (2 ml), was added 2-methylthioethylamine (3 ml) under nitrogen, and the resulting solution was stirred at 60° C. for 48 hours. The solution was poured into dichloromethane (20 ml), and washed with 1M potassium hydrogen sulphate, the aqueous layer was extracted with dichloromethane (3×15 ml). The combined organic layers were dried over Na$_2$SO$_4$, and then the solvent was evaporated. A white solid was obtained after column chromatography on silica gel using diethyl ether as eluent.

MS (Fab) m/z 422 (MH$^+$, 69), 322(52), 237(61), 118 (100), 57(30). $^1$HNMR (COdCl$_3$, 400 MHz) δ (ppm) 8.11–8.123 (m, 1H, ArH), 7.50–7.56 (m, 1H, CONH), 7.22–7.26 (m, 2H, ArH), 7.08–7.11 (m, 1H, ArH), 4.83–5.43 (m, 2H, NCHCO of indoline and NH of Abu), 4.13–4.21 (m, 1H, CH of Abu), 3.36–3.56 (m, 4H, CONHC$\underline{H}_2$CH$_2$ of indoline), 2.59–2.60 (m, 2H, CH$_2$S), 2.01 (s, 3H, SCH$_3$), 1.67–1.91 (m, 2H, C$\underline{H}_2$ of Abu), 1.45 (s, 9H, t-Bu), 1.06–1.192 (t, 3H, CH$_3$ of Abu).

1-(2(S)-Aminobutyryl)-indoline-2(S)-carboxylic acid(2-methylthioethyl) amide trifluoroacetate 1-(N-t-Butoxycarbonyl-2(S)-aminobutyryl)-indoline-2 (S)-carboxylic acid (2-methylthioethyl)amide (0.19 g, 0.45 mmol) was dissolved in dichloromethane (1.5 ml) in an ice-water bath, and trifluoroacetic acid (1.5 ml) was added under nitrogen. The solution was stirred at 0 to 5° C. until gas evolution ceased. The solution was evaporated to dryness in vacuo and the residue was treated with dried diethylether. A pink foam was obtained after flash column chromatography on silica gel using 20:1 dichloromethane: methanol as eluent.

m.p. 59.5–60.5° C.; MS (Fab) m/z 322 (MH$^+$, 10), 155 (35), 137(100). $^1$HNMR (DMSO-d$_6$, 400 MHz) δ (ppm) 8.60 (m, 1H, CONH), 8.25–8.36(m, 2H, acidic hydrogen), 8.14 (d, 1H, ArH), 7.22 –7.29, 7.08–7.12 (m, 3H, ArH), 5.03–5.06 (m, 1H, NCHCO of indoline), 3.15–3.73 (m, 13H, CH of Abu, CH$_2$ of indoline, CONHCH$_2$, overlap of H$_2$O), 2.53–2.73 (m, 2H, CH$_2$S), 2.06(s, 3H, SCH$_3$), 1.79–2.00 (m, 2H, CH$_2$ of Abu), 0.99 (t, 3H, CH$_3$ of Abu). IR (KBr) cm$^{-1}$ 3449(m), 3073 (w) (N—H, O—H); 1673(s), 1649(s) (C=O); 1596 (w), 1485 (m) (C=C); 1203(s), 1179(s), 1132(s) (C—O, C—N, C—F). Elemental Analysis: calculated for C$_{16}$H$_{23}$N$_3$O$_2$S, 1.2CF$_3$COOH, 0.5H$_2$O, C, 47.30, H, 5.44, N, 8.99%, found C, 47.32, H, 5.35, N, 8.97%.

EXAMPLE 4

Synthesis of 1-(2(S)-aminobutyryl)-indoline-2(S)-carboxylic acid N-(cyclopropylmethyl)amide trifluoroacetate 1-(N-t-Butoxycarbonyl-2(S)-aminobutyryl)-indoline-2(S)-carboxylic acid N-(cyclopropylmethyl)amide In a like manner to example 1, 1-(N-t-butoxycarbonyl-2 (S)-aminobutyryl)-indoline-2(S)-carboxylic acid (0.30 g, 0.8 mmol) and cyclopropylmethylamine hydrochloride (0.26 g, 2.5 mmol) were dissolved in dried dichloromethane (10 mL) under nitrogen at 0° C., and triethylamine (1.03 mL, 7.4 mmol) was added followed by bis(2-oxo-3-oxazolidinyl) phosphinic chloride (0.63 g, 2.5 mmol). The temperature was allowed to rise to room temperature and the mixture was stirred at room temperature for 24 hours, then poured into dichloromethane (25 mL) and washed (NaHCO$_3$). The organic was dried (Na$_2$SO$_4$) and evaporated to give an off white solid which was columned on silica gel using 8:2 dichloromethane: ethyl acetate as eluent, and then further purified by preparative hplc using 68% methanol.

MS(FAB) m/z 410 (MH$^+$); $^1$HNMR (DMSO 400 MHz): δ (ppm) 8.18–8.07 (m, 1H, NH of CONH), 7.34–7.01 (m, 4H, ArH), 5.47–4.78 (m, 1H, NCHCO of indoline), 4.104.21 (m, 1H, CH of Abu), 3.62–3.41, 3.34–2.98 (m, 3H, CH$_2$ of indoline & NH of CONH), 2.08–1.66 (m, >2H, CH$_2$ of Abu+H$_2$O), 1.52–1.34 (s, 9H, t-Bu of Boc), 1.19–0.99 (m, 3H, CH$_3$of Abu), 0.52–0.33, 0.221–0.09 (m, 5H, cyclopropane).

1-(2(S)-Aminobutyryl)-indoline-2(S)-carboxylic acid (N-cyclopropylmethyl)amide trifluoroacetate 1-(N-t-Butoxycarbonyl-2(S)-aminobutyryl)-indoline-2 (S)-carboxylic acid N-(cyclopropylmethyl)amide (20 mg, 0.04 mmol) was dissolved in dichloromethane (3 mL) in an ice-water bath, and trifluoroacetic acid (0.2 mL) was added under nitrogen. The solution was evaporated to dryness under vacuum and the residue was treated with dried diethyl ether. A very hygroscopic pale yellow foam was obtained after drying.

m.p. 57–74° C.; MS(FAB) m/z 302 (MH$^+$); $^1$HNMR (DMSO 400 MHz): δ (ppm) 8.09–8.17, 7.03–7.37 (m, 4H, ArH), 4.96–5.11 (m, 1H, NCHCO of indoline), 3.55–3.78 (m, >10H, CH of Abu & CH of CONHCH$_2$+D$_2$O), 2.87–3.17 (m, 3H, CH$_2$ of indoline & NH of CONH & CH of CONHCH$_2$), 1.75–2.02 (m, 2H, CH$_2$ of Abu), 0.88–1.15 (m, 3H, CH$_3$ of Abu), 0.36–0.49, 0.14–0.23 (m, 5H, cyclopropane). IR 3420(br, N—H, O—H, str overlapped by H$_2$O peak); 1675(s, C=O str); 1464(m, aromatic C=C); 1204(s, C—N str); 1135(s, C—O str); Elemental Analysis: calculated for C$_{17}$H$_{23}$N$_3$O$_2$; 1.4(CF$_3$CO$_2$H): C, 51.59; H, 5.33; N, 9.11%. Found: C, 51.66; H, 5.61; N, 8.90%.

EXAMPLE 5

Synthesis of 1-(2(S)-Aminobutyryl)-indoline-2(S)-carboxylic acid (2,2,2-trifluoroethyl)amide oxalate 1-(N-Benzyloxycarbonyl-2(S)-aminobutyryl)-indoline-2(S)-carboxylic acid To the solution of 1-(N-benzyloxycarbonyl-2(S)-aminobutyryl)-indoline-2(S)-carboxylic acid methyl ester (2.0 g, 5 mmol) in methanol (100 ml), was added lithium hydroxide(0.233 g, 5.5 mmol) in water (5 ml). The solution was stirred at 5–10° C. for 5 hours. The mixture was poured into dichloromethane (100 ml), and washed with cold potassium hydrogen sulphate (3×50 ml), water (50 ml). The organic layer was dried over sodium sulphate, and evaporated to provide a white foam which was pure enough for the next step.

MS (Fab) m/z 383(MH$^+$, 34), 254 (19), 163 (16), 118 (28), 91 (100). $^1$HNMR (CDCl$_3$, 400 MHz) δ (ppm) 8.24–8.29, 7.07–7.35(m, 9H, ArH), 5.97–6.02, 5.69–5.72, 4.70–5.31 (m, 6H, CH and NH of Abu, NCHCO of indoline, MS (Fab) m/z 330 (MH+, 100), 245(18), 118 (20), 95 (16), 58(52). $^1$HNMR (DMSO-d$_6$, 400 MHz) δ (ppm) 9.42–9.43, 8.92–9.00(m, 1H, CONH), 4.50–10.00 (acidic hydrogen overlap), 8.12–8.14 (m, 1H, ArH), 7.06–7.23 (m, 3H, ArH), 5.15–5.21, 4.60–4.69 (m, 1H, NCHCO of indoline), 3.62–4.01 (m, 5H, CH of Abu, CH$_2$ of indoline, CONHCH$_2$CF$_3$), 1.80–1.95 (m, 2H, CH$_2$ of Abu), 0.92–1.03 (m, 3H, CH$_3$ of Abu). IR (KBr) cm$^{-1}$ 3450(w), 3330 (w), 3232(w), 3069(w) (N—H, O—H), 1695(s), 1682(s), 1662 (s), 1651(s) (C=O), 1597(w), 1559(w), 1483(s) (C=C), 1276 (s), 1161(s) (C—O, C—N, C—F). Elemental Analysis: calculated for C$_{15}$H$_8$N$_3$O$_2$, (COOH)$_2$, 1.1H$_2$O, C, 46.49, H, 5.10, N, 9.57%, found C, 46.24, H, 5.04, N, 9.71%.

EXAMPLE 6

Synthesis of 1-(2(S)-aminobutyryl)-5-hydroxyindoline-2(R/S)-carboxylic acid (2,2,2,-trifluoroethyl)amide trifluoroacetate 5-Benzyloxyindoline-2(R/S)-carboxylic acid methylester 5-Benzyloxyindole-2-carboxylic acid ethylester (3 g, 10.1 mmol) and magnesium turnings (1.2 g, 50 mmol) were suspended in dried methanol (180 mL). This mixture was stirred at 5–10° C. under nitrogen for 3 hours, then poured into dichloromethane, and washed with saturated ammonium chloride solution. The organic layer was separated, and the aqueous layer was extracted with dichloromethane. The combined organic layers were dried over sodium sulphate and evaporated to leave a brown solid which was further purified by column chromatography (silica gel, dichloromethane) to afford a white solid.

$^1$HNMR (CDCl$_3$, 200 MHz) δ (ppm) 7.20–7.40 (m, 5H, ArH of Bn), 6.62–6.83 (m, 3H, ArH of indoline), 4.974 (s, 2H, CH$_2$Ph), 4.366 (dd, 1H, J$_1$=6.04 Hz, J$_2$=9.53 Hz, H2 of indoline), 3.749 (s, 3H, COOCH$_3$), 3.325 (m, 2H, H3 of indoline).

1-(N-t-Butoxycarbonyl-2(S)-aminobutyryl)-5-benzyloxyindoline-2(R/S)-carboxylic acid methylester CH$_2$Ph, COOH), 3.28–3.65(m, 2H, CH$_2$ of indoline), 1.66–2.06(m, 2H, CH$_2$ of Abu), 1.00–1.25(m, 3H, CH$_3$of Abu).

1-(N-Benzyloxycarbonyl-2(S)-aminobutyryl)-indoline-2(S)-carboxylic acid (2,2,2-trifluoroethyl) amide 1-(N-Benzyloxycarbonyl-2(S)-aminobutyryl)-indoline-2 (S)-carboxylic acid (0.382 g, 1 mmol) and 2,2,2-trifluoroethylamine hydrochloride (0.207 g, 1.5 mmol) were dissolved in dried dichloromethane (10 ml), and triethylamine (5.5 mmol) was added, followed by bis(2-oxo-3-oxazolidinyl)phosphinic chloride (0.508 g, 2.0 mmol) under nitrogen at 0° C. The temperature was allowed to rise to room temperature and the mixture was stirred at room temperature for 24 hours, then filtered. The filtrate was concentrated under reduced pressure to give a brown solid which was purified by column chromatography on silica gel using 7:3 petroleum spirit: ethyl acetate as eluent to afford a white solid.

m.p. 189.5–190.5° C. MS (Fab)m/z 464(MH$^+$, 100), 463 (17), 335(55), 244(29). $^1$HNMR (CDCl$_3$, 400 MHz) δ (ppm) 8.09–8.18, 7.60–7.68 (m, 1H, CONH), 7.10–7.36 (m, 9H, ArH), 4.88–5.60 (m, 4H, NCHCO of indoline and NH of Abu, CH$_2$Ph), 3.22–4.16(m, 5H, CH of Abu, CH$_2$ of indoline, CONHCH$_2$), 1.60–2.07 (m, 2H, CH$_2$of Abu), 1.05–1.13 (m, 3H, CH$_3$ of Abu).

1-(2(S)-Aminobutyryl)-indoline-2(S)-carboxylic acid (2,2,2-trifluoroethyl)amide oxalate 10% Palladium on activated carbon (20 mg) was added to the solution of 1-(N-benzyloxycarbonyl-2(S)-aminobutyryl)-indoline-2(S)-carboxylic acid (2,2,2-trifluoroethyl)amide (90 mg, 0.19 mmol) in methanol (10 ml), and the mixture was hydrogenated at 40 psi for 2.5 hours. After the catalyst was removed by filtration through celite, oxalic acid (18 mg) was added to the filtrate, and the solution was evaporated to dryness under reduced pressure at a bath temperature less than 50° C. The pure white crystalline product was obtained by recrystallization from dried diethyl ether-methanol (40:1).

m.p. 148.5–149.0° C.

1-(3,3-Dimethylaminopropyl)-3-ethylcarbodiimide methiodide (2.98 g, 11 mmol) was added to a cold solution (0° C.) of 5-benzyloxyindoline-2(R/S)-carboxylic acid methylester (2.83 g, 10 mmol) and N-t-butoxycarbonyl-2 (S)-aminobutyric acid (0.203 g, 11 mmol) in dichloromethane (20 mL) under nitrogen. The mixture was stirred at room temperature for 22 hours, then washed with 10% citric acid, water. The organic layer was separated, and aqueous layers were extracted with dichloromethane. The combined organic layers were dried and concentrated, and purified by column chromatography (silica gel, 1:1 petroleum spirit: diethyl ether), a white solid was obtained.

MS(FAB) m/z 510 (MH$^+$, 15), 509 (M$^+$, 26), 57 (100).

1-(N-t-Butoxycarbonyl-2(S)-aminobutyryl)-5-benzyloxyindoline-2(R/S)-carboxylic acid To a solution of 1-(N-t-butoxycarbonyl-2(S)-aminobutyryl)-5-benzyloxyindoline-2(R/S)-carboxylic acid methylester (2.75 g, 5.76 mmol) in methanol (20 mL), was added the water solution of sodium hydroxide (0.46 g, 11.52 mmol) under nitrogen at 10–15° C. The solution was stirred at room temperature for fourteen hours, then poured into dichloromethane and washed with potassium hydrogen sulphate solution, water. The organic layer was separated and dried over magnesium sulphate, solvent removal gave a yellow foam which was pure enough for the next step.

MS (FAB) m/z 477(MNa$^+$, 77), 455 (MH$^+$, 28), 399(40), 269(94), 178(91), 57(100).

1-(N-t-Butoxycarbonyl-2(S)-aminobutyryl)-5-benzyloxyindoline-2(R/S)-carboxylic acid (2,2,2-trifluoro)ethylamide Triethylamine (4.9 mL, 33 mmol) was added to the solution of 1-(N-t-butoxycarbonyl-2(S)-aminobutyryl)-5-benzyloxyindoline-2(S)-carboxylic acid (2.6 g, 5.72 mmol)

and 2,2,2-trifluoroethylamine hydrochloride (1.55 g, 11.4 mmol) in dried dichloromethane (50 mL) at 0° C. under nitrogen, followed by bis(2-oxo-3-oxazolidinyl)phosphinic chloride (2.902 g, 11.4 mmol). The temperature was allowed to rise to room temperature and the mixture was stirred at room temperature for twenty-four hours, then filtered. The filtrate was concentrated under vacuum to give a brown solid which was purified by column chromatography (silica gel, 8:2 diethyl ether: petroleum spirit) to provide a white solid as the desired product.

MS (FAB) m/z 536(MH$^+$, 26), 535(34), 350(64), 259(67), 91(89), 57(85).

1-(N-t-Butoxycarbonyl-2(S)-aminobutyryl)-5-hydroxyindoline-2(R/S)-carboxylic acid 2,2,2-trifluoroethylamide A mixture of 1-(N-t-butoxycarbonyl-2(S)-aminobutyryl)-5-benzyloxyindoline-2(R/S)-carboxylic acid 2,2,2-trifluoroethylamide (0.9 g, 1.68 mmol) and palladium on activated carbon (0.1 g, 10% wet) in ethyl acetate (20 mL) was hydrogenated under 30 psi hydrogen at room temperature overnight. Then the catalyst was removed by filtration over celite, and the filtrate was evaporated to provide a white solid.

MS (FAB) m/z 468(MNa$^+$, 23), 445 (MH$^+$, 13), 346 (31), 260 (88), 134 (100); $^1$HNMR (CDCl$_3$, 300 MHz) δ (ppm) 8.30–8.35 (m, 1H, CONH), 7.50–7.90 (m, 1H, ArH), 6.40–4.73 (m, 2H, ArH), 5.20–5.52 (m, 2H, OH, H2 of indoline), 4.80–5.05 (m, 1H, NH of Abu), 3.70–4.20 (m, 3H, CH$_2$CF$_3$, CH of Abu), 3.00–3.55 (m, 2H, H3 of indoline), 0.80–2.00 (m, 14H, CH$_2$ of Abu, t-Bu, CH$_3$ of Abu).

1-(2(S)-Aminobutyryl)-5-hydroxyindoline-2(R/S)-carboxylic acid (2,2,2-trifluoro)ethylamide trifluoroacetate Trifluoroacetic acid (0.8 mL) was added dropwise to the solution of 1-(N-t-butoxycarbonyl-2(S)-aminobutyryl)-5-hydroxyindoline-2(R/S)-carboxylic acid (2,2,2-trifluoro)ethylamide (200 mg, 0.44 mmol) in dichloromethane (1 mL) in an ice-water bath under nitrogen. This solution was stirred at 0–5° C. until gas evolution ceased, then evaporated to dryness under vacuum below 45° C., and the residue was treated with dried diethyl ether to give a brown foam.

m.p. 76–88° C.; MS (FAB) m/z 691(2MH$^+$, 7), 346 (MH$^+$, 100), 261(31), 154(27), 58(64); $^1$HNMR (DMSO-d$_6$, 400 MHz) δ (ppm) 9.00–9.20, 8.7–8.85 (m, 1H, CONH), 8.18–8.40 (m, 2H, acidic H), 7.92, 7.84 (d, 1H, J=9 Hz, ArH), 6.5–6.75 (m, 2H, ArH), 5.2–5.3, 5.0–5.1 (m, 1H, H2 of indoline), 3.35–4.10 (m, 5H, CH$_2$CF$_3$, OH, CH of Abu, one H3 of indoline), 2.75–3.05 (m, 1H, one H3 of indoline), 1.55–2.05(m, 2H, CH$_2$ of Abu), 1.01, 0.95, 0.87 (3t, 3H, J=7.3 Hz, CH$_3$ of Abu). IR (KBr disc) cm$^{-1}$ 3291, 3090, 2970(broad, m) (N—H, O—H); 1674(vs), 1675(vs) (C=O); 1620(w), 1490(m) (C=C); 1275(vs), 1160(s) (C—O, C—N, C—F). Elemental Analysis: calculated for C$_{15}$H$_{18}$F$_3$N$_3$O$_3$, 1.8CF$_3$COOH: C, 40.58; H, 3.62; N, 7.63%. Found: C, 40.29; H, 3.70; N, 7.63%.

EXAMPLE 7

Synthesis of 1-(2(S)-aminobutyryl)-4-chloroindoline-2(R/S)-carboxylic acid (2,2,2-trifluoroethyl)amide trifluoroacetate

Methyl azidoacetate

A solution of methyl bromoacetate (150 g, 0.901 mol ) in dry acetonitrile (800 ml) was treated with sodium azide (58.57 g, 0.901 mol) under nitrogen and the mixture was heated for 20 hours at reflux. After cooling, water (150 ml) was added and the mixture was stirred for half an hour. The top layer was separated and the bottom layer was treated with salt and extracted with diethyl ether. The organic phases were combined and solvent removed in vacuum at a bath temperature not exceeding 50° C. to give a yellow oil which was used for the next step without further purification.

$^1$HNMR (CDCl$_3$, 200 MHz) δ(ppm) 3.87(s, 2H, CH$_2$), 3.79 (s, 3H, OCH$_3$).

Methyl 2-azido-3-(2-chlorophenyl)propenoate

Sodium pieces(3.678 g, 160 mmol) were added in portions to methanol (200 ml) over a 30 minute period. The resulting solution was cooled in a dry ice/acetone bath to −18° C. and then over one hour a mixture of 2-chlorobenzaldehyde (4.832 g, 40 mmol) and methyl azidoacetate (160 mmol) was added at a rate that maintained the temperature below −15° C. After three hours, the solution was stored at 5° C. for two days to give crystalline material which was collected by filtration and washed with cold hexane to give pure product as a yellow crystals.

$^1$HNMR(CDCl$_3$, 200 MHz), δ(ppm) 8.15–8.20 (m, 1H, ArCH=), 7.24–7.43 (m, 4H, ArH), 3.93 (s, 3H, OCH$_3$).

4-Chloroindole-2-carboxylic acid methyl ester

Methyl 2-azido-3-(2-chlorophenyl)-propenoate (3.566 g, 144 mmol) was suspended in toluene (800 ml) and the mixture was heated at reflux for three hours, then cooled and allowed to stir at room temperature overnight. A yellow crystalline material was obtained by filtration and recrystallised from hexane.

MS (FAB) m/z 210(MH$^+$, 43), 209 ((68), 139 (94), 77(100). $^1$HNMR(CDCl$_3$, 200 MHz) δ (ppm) 9.06–9.16(m, 1H, H—N), 7.18–7.40 (m, 4H, H—Ar), 3.98(s, 3H, OCH$_3$).

4-Chloroindoline-2(R/S)-carboxylic acid methyl ester

4-Chloroindole-2-carboxylic acid methyl ester (0.8 g, 3.8 mmol) and magnesium turnings (0.37 g, 15.2 mmol) were suspended in dried methanol (50 ml). This mixture was stirred at 5 to 10° C. under nitrogen for 3 hours, then poured into dichloromethane (200 ml), and washed with saturated ammonium chloride solution. The organic layer was separated, and the aqueous layer was extracted with dichloromethane (3×100 ml). The combined organic layers were dried over sodium sulphate and evaporated. A brown solid was obtained. After column chromatography on silica gel using dichloromethane as eluent, a yellow oil was obtained.

MS (Fab) m/z 212 (MH$^+$, 73), 211 (M, 84), 152(100). $^1$HNMR (CDCl$_3$, 400 MHz) δ (ppm) 6.99–7.05(m, 2H, ArH ), 6.58 (m, 1H, ArH), 4.53–4.62(m, 1H, NH of indoline), 4.424.46(m, 1H, NCHCO of indoline), 3.76 (s, 3H, OCH$_3$), 3.31–3.42 (m, 2H, CH$_2$ of indoline).

1-(N-t-Butoxycarbonyl-2(S)-aminobutyryl)-4-chloroindoline-2(R/S)-carboxylic acid methyl ester To a solution of 4-chloroindoline-2(R/S)-carboxylic acid methyl ester (0.41 g, 1.94 mmol) and N-t-butoxycarbonyl-2(S)-aminobutyric acid (0.47 g, 2.33 mmol) dissolved in dried dichloromethane(10 ml) under nitrogen at 10° C., was added diisopropylcarbodiimide (0.36 ml, 2.33 mmol). The mixture was stirred at room temperature for 24 hours, then filtered. The filtrate was evaporated under vacuum to afford a brown solid which was purified by column chromatography on silica gel using 20:1 dichloromethane: diethyl ether as eluent. A white foam was obtained which was the mixture of two diastereomers.

MS (Fab) m/z 397 (MH⁺, 15), 330(40), 189(95), 145 (100); ¹HNMR (CDCl₃, 400 MHz) δ (ppm) 8.06–8.17(dd, 1H, ArH), 7.04–7.27 (m, 2H, ArH), 4.94–5.41 (m, 2H, NCHCO of indoline, NH of Abu), 4.27–4.59 (m, 1H, CH of Abu), 3.79, 3.16 (2S, 3H, OCH₃), 0.87–2.0 (m, CH₂ of Abu, t-Bu, CH₃ of Abu).

1-(N-t-Butoxycarbonyl-2(S)-aminobutyryl)-4-chloroindoline-2(R/S)-carboxylic acid To the solution of 1-(N-t-butoxycarbonyl-2(S)-aminobutyryl)4-chloroindoline-2(R/S)-carboxylic acid methyl ester (0.38 g, 0.96 mmol) in methanol (10 ml), was added sodium hydroxide(0.046 g, 1.15 mmol) in water (4 ml). The solution was stirred at 5 to 10° C. for 4 hours. The mixture was poured into dichloromethane (20 ml), and washed with cold potassium hydrogen sulphate (3×20 ml), and water (20 ml). The organic layer was dried over sodium sulphate, and evaporated to provide a white foam which was pure enough for the next step.

MS (Fab) m/z 405(MNa⁺, 36), 330(35), 189(30), 145 (100) 89(60); ¹HNMR (CDCl₃, 400 MHz) δ (ppm) 8.16 (2d, 1H, ArH), 7.06–7.27(m, 2H, ArH), 4.80–6.20(m, COOH overlap), 5.68–5.70 (m, 1H, NCHCO of indoline), 5.06–5.09 (m, 1H, NH of Abu), 4.664.86 (m, 1H, CH of Abu), 4.204.30, 3.56–3.75 (m, 2H, CH₂ of indoline), 0.84–2.05(m, 14H, CH₂ of Abu, t-Bu, CH₃ of Abu).

1-(N-t-Butoxycarbonyl-2(S)-aminobutyryl )4-chloroindoline-2(R/S)-carboxylic acid (2,2,2-trifluoroethyl)amide 1-(N-t-Butoxycarbonyl-2(S)-aminobutyryl)-4-chloroindoline-2(S)-carboxylic acid (0.2 g, 0.52 mmol) and 2,2,2-trifluoroethylamine hydrochloride (0.142 g, 1.0 mmol) were dissolved in dried dichloromethane (10 ml) under nitrogen at 0° C., and triethylamine (0.44 ml, 3 mmol) was added followed by bis(2-oxo-3-oxazolidinyl)phosphinic chloride (0.265 g, 1.0 mmol). The temperature was allowed to rise to room temperature and the mixture was stirred at room temperature for 24 hours, then filtered. The filtrate was concentrated under vacuum to give a brown solid which was columned on silica gel using 95:5 dichloromethane: diethyl ether as eluent to provide a white solid as the desired product.

MS (Fab) m/z486(MNa⁺, 25), 408(20), 364(30), 280(35), 152(100); ¹HNMR (CDCl₃, 400 MHz) δ (ppm) 7.92–8.30 (m, 1H, CONH), 6.85–7.55(m, 3H, ArH), 4.85–5.50 (m, 2H, NCHCO of indoline and NH of Abu), 3.18–4.15 (m, 5H, CH of Abu, CH₂ of indoline, CH₂CF₃), 1.44–2.00 (m, 2H, CH₂ of Abu), 1.44 (s, 9H, t-Bu), 0.87–1.39 (m, 3H, CH₃ of Abu).

1-(2(S)-Aminobutyryl)-4-chloroindoline-2(R/S)-carboxylic acid (2,2,2-trifluoroethyl)amide trifluoroacetate 1-(N-t-Butoxycarbonyl-2(S)-aminobutyryl)4-chloroindoline-2(R/S)-carboxylic acid (2,2,2-trifluoroethyl) amide (70 mg, 0.15 mmol) was dissolved in dichloromethane (1 ml) in an ice-water bath, and trifluoroacetic acid (1 ml) was added under nitrogen. The solution was stirred at 0 to 5° C. until gas evolution ceased. The solution was evaporated to dryness in vacuo and the residue was treated with dried diethyl ether. A white foam was obtained after column chromatography on flash silica gel by using 20:1 dichloromethane:methanol as eluent.

m.p. 104–106° C. MS (Fab) m/z 386(MNa⁺, 40), 364 (MH⁺, 100), 152(60). ¹HNMR (DMSO-d₆, 400 MHz) δ (ppm) 9.10–9.26 (m, 1H, CONH), 8.02–8.10 (m, 1H, ArH), 7.08–7.40(m, 2H, ArH), 5.25–5.40 (m, 1H, NCHCO of indoline), 2.96–4.10 (m, 5H, CH₂CF₃, CH of Abu, CH₂ of indoline, H₂O), 1.60–1.90(m, 2H, CH₂ of Abu), 0.95, 0.84 (2t, 3H, CH₃ of Abu). IR (KBr) cm⁻¹ 3370 (broad, w) (N—H, O—H); 1730(vs), 1670 (vs), 1650(m) (C=O); 1590(s) 1470(m), (C=C); 1205(s), 1162(vs), 1130(s) (C—O, C—N, C—F). Elemental Analysis: calculated for C₁₅H₁₇ClF₃N₃O₂, 1.2CF₃COOH, 0.5H₂O C, 41.01, H, 3.80, N, 8.25%, found C, 40.92, H, 3.81, N, 8.10%.

EXAMPLE 8

Synthesis of 1-(2(S)-aminobutyryl)-4-fluoroindoline-2(R/S)-carboxylic acid (2,2,2-trifluoroethyl)amide trifluoroacetate 4-Fluoroindole-2-carboxylic acid To a mixture of potassium ethoxide (5.317 g, 63 mmol) in diethyl ether (250 ml), ethyl oxalate (8.65 ml, 63 mmol) was added. After the solid ethoxide disappeared, 2-fluoro-6-nitrotoluene (10 g, 63.18 mmol) in diethyl ether (20 ml) was added, and the mixture was stirred at 35 to 38° C. for eighteen hours. Water (200 ml) was added, and the aqueous layer separated from the ether layer. The deep red aqueous solution was washed with ether (2×30 ml) to remove the unchanged starting materials, and acidified with a slight excess of hydrochloric acid, then the aqueous layer was extracted with ethyl acetate (3×100 ml). The combined ethyl acetate layers were evaporated and a brown solid was obtained which gave a yellow solid after recrystallization from acetic acid. This yellow solid was dissolved in ammonia (70 ml, d=0.88 diluted to 100 ml with water), then a hot solution of ferrous sulphate (90 g of hydrated crystals in 100 ml of water) added, and the mixture was stirred on a water bath for an hour. After cooling, the black sludge of ferric hydroxide was filtered off and washed well with warm water containing a little ammonia until a test portion gave only a faint milkiness on acidification. The filtration and washings were concentrated, the solution acidified and extracted with ethyl acetate. The organic layer was concentrated to give a brown solid as the desired product.

4-Fluoroindole-2-carboxylic acid methyl ester 25 4-Fluoroindole-2-carboxylic acid (0.65 g, 3.40 mmol) was dissolved in methanol (50 ml), and 4-toluenesulfonic acid (1.4 g, 7.36 mmol) was added under nitrogen. The solution was stirred at reflux for 24 hours. Most of the methanol was removed by evaporation, and the residue was dissolved in dicholoromethane (100 ml), washed with saturated sodium carbonate, and the organic layer was separated. The aqueous layer was extracted with dichloromethane (3×50 ml). The combined organic layers were washed with water, dried over sodium sulphate, and evaporated to yield a yellow crystalline material.

MS(EI) m/z 193(M⁺, 65), 161(100), 133(50), 107(35); ¹HNMR(CDCl₃, 200MHz), δ (ppm) 8.90–9.10(m, 1H, NH of indole), 7.20–7.30 (m, 2H, ArH), 6.76–6.85(m, 1H, ArH,), 3.95(s, 1H, OCH₃).

4-Fluoroindoline-2(R/S)-carboxylic acid methyl ester

4-Fluoroindole-2-carboxylic acid methyl ester (0.52 g, 2.7 mmol) and magnesium turnings (0.136 g, 5.6 mmol) were suspended in dried methanol (30 ml). This mixture was stirred at 5 to 10° C. under nitrogen for 3 hours, then poured into dichloromethane (100 ml), and washed with saturated ammonium chloride solution. The organic layer was separated, and the aqueous layer was extracted with dichloromethane (3×40 ml). The combined organic layers were dried over sodium sulphate and evaporated. A brown solid was obtained. After column chromatography on silica gel using dichloromethane as eluent, a reddish oil was obtained.

MS(EI) m/z 195(M+, 17), 172(20), 136(100), 109(40); $^1$HNMR (CDCl$_3$, 200 MHz) δ (ppm) 7.01–7.03(m, 1H, H-Ar), 6.42–6.50(m, 2H, ArH), 4.424.58 (m, 2H, NH and NCHCO of indoline), 3.78 (s, 3H, OCH$_3$), 3.39–3.41 (m, 2H, CH$_2$ of indoline).

1-(N-t-Butoxycarbonyl-2(S)-aminobutyryl)-4-fluoroindoline-2(R/S)-carboxylic acid methyl ester To a solution of 4-fluoroindoline-2(R/S)-carboxylic acid methyl ester (0.43 g, 2.205 mmol) and N-t-butoxycarbonyl-2(S)-aminobutyric acid (0.47 g, 2.33 mmol) dissolved in dried dichloromethane(10 ml) under nitrogen at 10° C., was added diisopropylcarbodiimide (0.36 ml, 2.33 mmol). The mixture was stirred at room temperature for 24 hours, then filtered. The filtrate was evaporated under vacuum to afford a brown solid which was purified by column chromatography on silica gel using 10:1 dichloromethane: diethyl ether as eluent. An off-white foam was obtained which was the mixture of the two diastereomers.

MS (EI) m/z 381 (M+), 307(10), 195(80), 136(100), 57(96); $^1$HNMR (CDCl$_3$, 300 MHz) δ (ppm) 7.90–8.12(2d, 1H, ArH), 7.10–7.20 (m, 1H, ArH), 6.70–7.00(m, 1H, ArH), 4.90–5.50 (m, 2H, NCHCO of indoline and NH of Abu), 4.10–4.45 (m, 1H, CH of Abu), 3.80, 3.72 (2s, 3H, OCH$_3$), 3.37–3.65, 3.10–3.25 (m, 2H, CH$_2$ of indoline), 1.50–1.95 (m, 2H, CH$_2$ of Abu), 1.45 (s, 9H, t-Bu), 0.90–1.30 (m, 3H, CH$_3$ of Abu).

1-N-t-Butoxycarbonyl-2(S)-aminobutyryl)4-fluoroindoline-2(R/S)-carboxylic acid

To the solution of 1-(N-t-butoxycarbonyl-2(S)-aminobutyryl)-4-fluoroindoline-2(R/S)-carboxylic acid methyl ester (0.27 g, 0.71 mmol) in methanol (10 ml), was added sodium hydroxide (0.028 g, 0.71 mmol) in water (4 ml). The solution was stirred at 5 to 10° C. for 4 hours. The mixture was poured into dichloromethane (20 ml), and washed with cold potassium hydrogen sulphate (3×20 ml), and water (20 ml). The organic layer was dried over sodium sulphate, and evaporated to provide a white foam which was pure enough for the next reaction.

MS (Fab) m/z 389(MNa+, 100), 311(60), 182(55), 136 (52), 136(52), 57(75); $^1$HNMR (CDCl$_3$, 400 MHz) δ (ppm) 7.92–8.05(m, 1H, ArH), 6.30–7.28 (m, 3H; ArH, COOH), 5.60–5.75(dd, 1H, NCHCO of indoline), 5.03–5.20 (m, 1H, NH of Abu), 4.624.74 (m, 1H, CH of Abu), 3.25–3.65 (m, 2H, CH$_2$ of indoline), 0.85–2.05(m, 14H, CH$_2$ of Abu, t-Bu, CH$_3$ of Abu).

1-(N-t-Butoxycarbonyl-2(S)-aminobutyryl)-4-fluoroindoline-2(R/S)-carboxylic acid (2,2,2-trifluoroethyl)amide 1-(N-t-Butoxycarbonyl-2(S)-aminobutyryl)4-fluoroindoline-2(S)-carboxylic acid (0.12 g, 0.32 mmol) and 2,2,2-trifluoroethylamine hydrochloride (0.136 g, 1.0 mmol) were dissolved in dried dichloromethane (10 ml) under nitrogen at 0° C., and triethylamine (0.44 ml, 3 mmol) was added followed by bis(2-oxo-3-oxazolidinyl)phosphinic chloride (0.265 g, 1.0 mmol). The temperature was allowed to rise to room temperature and the mixture was stirred at room temperature for 24 hours, then filtered. The filtrate was concentrated under vacuum to give a brown solid. A white solid was obtained by column chromatography on silica gel using 7:3 petroleum spirit: ethyl acetate as eluent followed by recrystallization from diethyl ether.

MS (Fab) m/z 448(MH+, 25), 392(30), 154(100), 137(59) $^1$HNMR (CDCl$_3$, 400 MHz) δ (ppm) 8.17–8.30(m, 1H, CONH), 7.65–7.95(m, 1H, ArH), 7.12–7.25, 6.73–6.90(m, 2H, ArH), 4.80–5.40 (m, 2H, NCHCO of indoline and NH of Abu), 3.15–4.20(m, 5H, CH of Abu, NCHCO of indoline, CH$_2$CF$_3$), 0.86–2.00(m, 14H, CH$_2$of Abu, t-Bu, CH$_3$ of Abu).

1-(2(S)-Aminobutyryl)-4-fluoroindoline-2(R/S)-carboxylic acid (2,2,2-trifluoroethyl)amide trifluoroacetate 1-(N-t-Butoxycarbonyl-2(S)-aminobutyryl)4-fluoroindoline-2(R/S)-carboxylic acid (2,2,2-trifluoroethyl) amide (80 mg, 0.179 mmol) was dissolved in dichloromethane (1 ml) in an ice-water bath, and trifluoroacetic acid (0.8 ml) was added under nitrogen. The solution was stirred at 0 to 5° C. until gas evolution ceased. The solution was evaporated to dryness in vacuo and the residue was treated with dried ether. A white foam was obtained after column chromatography on flash silica gel by using 20:1 dichloromethane:methanol as eluent.

m.p. 57.5–58.5° C. MS (Fab) m/z 348 (MH+, 100), $^1$HNMR (DMSO$_6$, 400 MHz) δ (ppm) 9.25–9.30 (m, 1H, CONH), 8.28–8.49 (m, 3H, acidic H), 7.97(d, 1H, ArH), 7.26–7.40, 6.93–7.05(m, 2H, ArH), 5.15–5.29 (dd, 1H, NCHCO of indoline), 3.10–4.10 (m, 10H, CH$_2$CF$_3$, CH of Abu, CH$_2$ of indoline, H$_2$O), 1.75–2.05(m, 2H, CH$_2$ of Abu), 1.03, 0.98 (2t, 3H, CH$_3$ of Abu). IR (KBr) cm$^{-1}$ 3443(broad, w), (N—H, O—H); 1686(vs), 1671 (vs) (C=O); 1601(w), 1472(m) (C=C); 1208(vs), 1168(vs), 1143(s) (C—O, C—N, C—F). Elemental Analysis: calculated for C$_{15}$H$_{17}$F$_4$N$_3$O$_2$, 2.5CF$_3$COOH, C, 37.99, H, 3.11, N, 6.64%, found C, 38.14, H, 3.03, N, 6.39%.

EXAMPLE 9

Synthesis of 1-(2(S)-aminobutyryl)-5-methoxyindoline-2(R/S)-carboxylic acid (2,2,2-trifluoroethyl)amide trifluoroacetate 5-Methoxyindoline-2(R/S)-carboxylic acid methyl ester 5-Methoxyindole-2-carboxylic acid ethyl ester (2 g, 9.13 mmol) and magnesium turnings (0.432 g, 18 mmol) were suspended in dried methanol (30 ml). This mixture was stirred at 5 to 10° C. under nitrogen for 3 hours, then poured into dichloromethane (200 ml), and washed with saturated ammonium chloride solution. The organic layer was separated, and the aqueous layer was extracted with dichloromethane (3×100 ml). The combined organic layers were dried over sodium sulphate and evaporated. A brown solid was obtained. After column chromatography on silica gel using dichloromethane as eluent, a brown solid was obtained.

$^1$HNMR (CDCl$_3$, 400 MHz) δ (ppm) 6.62–6.72(m, 3H, ArH ), 4.23–4.39(m, 2H, NCHCO and NH of indoline), 3.76 (s, 3H, COOCH$_3$), 3.74 (s, 3H, ArOCH$_3$), 3.29–3.42 (m, 2H, CH$_2$ of indoline).

1-(N-t-Butoxycarbonyl-2(S)-aminobutyryl)-5-methoxyindoline-2(R/S)-carboxylic acid methyl ester To a solution of 5-methoxyindoline-2(R/S)-carboxylic acid methyl ester (1.5 g, 7.23 mmol) and N-t-butoxycarbonyl-2(S)-aminobutyric acid (1.62 g, 7.96 mmol) dissolved in dried dichloromethane (15 ml) under nitrogen at 10° C., was added diisopropylcarbodiimide (1.00 ml, 7.96 mmol). The mixture was stirred at room temperature for 24 hours, then filtered. The filtrate was evaporated under vacuum to afford a brown solid which was purified by column chromatography on silica gel using dichloromethane as eluent. A white foam was obtained which was the mixture of two diastereomers.

MS (Fab) m/z 393 (MH$^+$, 14), 207(76), 148(61), 57(100); $^1$HNMR (CDCl$_3$, 400 MHz) δ (ppm) 8.05–8.19 (2d, 1H, ArH), 6.70–6.76 (m, 2H, ArH), 4.88–5.70(m, 2H, NCHCO of indoline, NH of Abu), 4.16–4.40 (m, 1H, CH of Abu), 3.71–3.76(m, 6H, COOCH$_3$, ArOCH$_3$), 3.00–3.65 (m, 2H, CH$_2$ of indoline), 1.55–2.05(m, 2H, CH$_2$ of Abu), 1.46, 1.42, 1.41 (3s, 9H, t-Bu), 1.08, 0.96, 0.90 (3t, 3H, CH$_3$ of Abu).

1-(N-t-Butoxycarbonyl-2(S)-aminobutyryl)-5-methoxyindoline-2(R/S)-carboxylic acid To the solution of 1-(N-t-butoxycarbonyl-2(S)-aminobutyryl)-5-methoxyindoline-2(R/S)-carboxylic acid methyl ester (1.3 g, 3.3 mmol) in methanol (20 ml), was added sodium hydroxide(0.265 g, 6.6 mmol) in water (10 ml). The solution was stirred at 5 to 10° C. for 4 hours. The mixture was poured into dichloromethane (40 ml), and washed with cold potassium hydrogen sulphate (3×20 ml), and water (20 ml). The organic layer was dried over sodium sulphate, and evaporated to provide a white foam which was pure enough for the next step.

MS (Fab) m/z 379(MH+, 10), 323(16), 193(61), 145(70), 57(100); $^1$HNMR (CDCl$_3$, 400 MHz) δ (ppm) 8.05–8.10 (m, 1H, ArH), 6.70–7.05 (m, 2H, ArH), 4.90–5.75 (m, 2H, NCHCO of indoline, NH of Abu), 4.20–4.70 (m, 1H, CH of Abu), 3.76 (s, 3H, ArOCH$_3$), 3.30–3.75 (m, 2H, CH$_2$ of indoline), 0.80–2.05 (m, 14H, CH$_2$ of Abu, t-Bu, CH$_3$ of Abu).

1-(N-t-Butoxycarbonyl-2(S)-aminobutyryl)-5-methoxyindoline-2(R/S)-carboxylic acid (2,2,2-trifluoroethyl)amide 1-(N-t-Butoxycarbonyl-2(S)-aminobutyryl)-5-methoxyindoline-2(S)-carboxylic acid (0.38 g, 1 mmol) and 2,2,2-trifluoroethylamine hydrochloride (0.271 g, 2.0 mmol) were dissolved in dried dichloromethane (20 ml) under nitrogen at 0° C., and triethylamine (0.7 ml, 5 mmol) was added followed by bis(2-oxo-3-oxazolidinyl)phosphinic chloride (0.509 g, 2 mmol). The temperature was allowed to rise to room temperature and the mixture was stirred at room temperature for 24 hours, then filtered. The filtrate was concentrated under vacuum to give a brown solid which was columned on silica gel using 7:3 petroleum spirit:ethyl acetate as eluent to provide a white solid as the desired product.

MS (Fab) m/z 460(MH$^+$, 14), 360(14), 274(60), 148(100), 57(81); $^1$HNMR (CDCl$_3$, 300 MHz) δ (ppm) 7.96–8.25(m, 1H, CONH), 7.42–7.65(m, 1H, ArH), 6.55–7.00(m, 2H, ArH), 4.80–5.60(m, 4H, NCHCO of indoline, NH of Abu, CH$_2$CF$_3$), 3.85–4.10 (m, 1H, CH of Abu), 3.80(s, 3H, ArOCH$_3$), 3.20–370(m, 2H, CH$_2$ of indoline), 0.84–2.00 (m, 14H, CH$_2$of Abu, t-Bu, CH$_3$ of Abu). Elemental analysis: calculated for C$_{21}$H$_{28}$F$_3$N$_3$O$_5$ C, 54.9, H, 6.14, N, 9.15%, found C, 54.79, H, 6.38, N, 9.09%

1-(2(S)-Aminobutyryl)-5-methoxyindoline-2(R/S)-carboxylic acid (2,2,2-trifluoroethyl)amide trifluoroacetate 1-(N-t-Butoxycarbonyl-2(S)-aminobutyryl)-5-methoxyindoline-2(R/S)-carboxylic acid (2,2,2-trifluoroethyl)amide (0.2 mg, 0.435 mmol) was dissolved in dichloromethane (2 ml) in an ice-water bath, and trifluoro-acetic acid (1 ml) was added under nitrogen. The solution was stirred at 0 to 5° C. until gas evolution ceased. The solution was evaporated to dryness in vacuo and the residue was treated with dried diethyl ether. A purple foam was obtained which was the mixture of two diastereomers (30:70).

m.p. 63.5–66° C.; MS (Fab) m/z 719(2MH$^+$, 15), 360 (MH$^+$, 100), 275(50), 148(45), 58(80); $^1$HNMR (DMSO-d$_6$, 400 MHz) δ (ppm) 9.20–9.30 (m, 1H, CONH), 8.15–8.50 (m, 3H, acidic H), 7.92–8.10 (2d, 1H, ArH), 6.75–7.15 (m, 2H, ArH), 5.00–5.30(dd, 1H, NCHCO of indoline), 3.40–4.10(m, 7H, CH$_2$CF$_3$, OCH$_3$, CH of Abu, one CH$_2$ of indoline), 2.86–3.15 (m, 1H, one CH$_2$ of indoline), 1.50–2.00 (m, 2H, CH$_2$ of Abu), 0.70–1.23 (m, 3H, CH$_3$ of Abu). IR (KBr) cm$^{-1}$ 3403 (broad, w)(N—H, O—H); 1670 (vs), 1664(vs) (C═O); 1616(w), 1491(m) (C═C); 1205 (vs), 1167(vs), 1160(s) (C—O, C—N, C—F). Elemental Analysis: calculated for C$_{16}$H$_{20}$F$_3$N$_3$O$_3$, 1.4CF$_3$COOH, 0.6H$_2$O, C, 342.62, H, 34.30, N, 7.93%, found C, 42.61, H, 4.30, N, 7.86%.

EXAMPLE 10

Synthesis of 1-(2(S)-aminobutyryl)-5-trifluoromethoxyindoline-2(R/S)-carboxylic acid (2,2,2-trifluoroethyl)amide trifluoroacetate 5-Trifluoromethoxyindoline-2(R/S)-carboxylic acid methyl ester 5-Trifluoromethoxyindole-2-carboxylic acid ethyl ester (2.25 g, 8.24 mmol) and magnesium turnings (0.50 g, 21.7 mmol) were suspended in dried methanol (60 ml). This mixture was stirred at 5 to 10° C. under nitrogen for 3 hours, then poured into dichloromethane (200 ml), and washed with saturated ammonium chloride solution. The organic layer was separated, and the aqueous layer was extracted with dichloromethane (3×100 ml). The combined organic layers were dried over sodium sulphate and evaporated. A brown solid was obtained. After column chromatography on silica gel using dichloromethane as eluent, a brown solid was obtained.

MS (EI) m/z 261 (M$^+$, 28), 231(46), 214(20), 202(100), 116(51); $^1$HNMR (CDCl$_3$, 400 MHz) δ (ppm) 6.88–6.96(m, 2H, ArH), 6.65–6.68(m, 1H, ArH), 4.40–4.50(m, 2H, NCHCO and NH of indoline), 3.78 (s, 3H, COOCH$_3$), 3.29–3.42 (m, 2H, CH$_2$ of indoline).

1-(N-t-Butoxycarbonyl-2(S)-aminobutyryl)-5-trifluoromethoxyindoline-2(R/S)-carboxylic acid methyl ester To a solution of 5-trifluoromethoxyindoline-2(R/S)-carboxylic acid methyl ester (1.95 g, 7.47 mmol) and N-t-butoxycarbonyl-2(S)-aminobutyric acid (1.52 g, 7.47 mmol) dissolved in dried dichloromethane (15 ml) under nitrogen at 10° C., was added diisopropylcarbodiimide (1.00 ml, 7.96 mmol). The mixture was stirred at room temperature for 24 hours, then filtered. The filtrate was evaporated under vacuum to afford a brown oil which was purified by column chromatography on silica gel first by using 95:5 dichloromethane: diethyl ether as eluent, then another column on silica gel by using 7:3 petroleum spirit: diethyl ether. A yellow foam was obtained which was the mixture of two diastereomers.

MS (Fab ) m/z 447 (MH$^+$, 31), 391(80), 347(56), 261 (100), 202(99); $^1$HNMR (CDCl$_3$, 300 MHz) δ (ppm) 8.15–8.32 (2d, 1H, ArH), 7.05–7.15 (m, 2H ArH), 5.25–5.45 (m, 1H, NCHCO of indoline), 4.90–5.10 (m, 1H, NH of Abu), 4.15–4.45 (m, 1H, CH of Abu), 3.74, 3.80, 3.82 (3s, 3H, COOCH$_3$), 3.30–3.70 (m, 2H, CH$_2$ of indoline), 1.65–2.05 (m, 2H, CH$_2$ of Abu), 1.46, 1.42 (2s, 9H, t-Bu), 0.80–1.20 (m, 3H, CH$_3$ of Abu).

1-(N-t-Butoxycarbonyl-2(S)-aminobutyryl)-5-trifluoromethoxyindoline-2(R/S)-carboxylic acid To the solution of 1-(N-t-butoxycarbonyl-2(S)-aminobutyryl)-5-trifluoromethoxyindoline-2(R/S)-carboxylic acid methyl ester (1.0 g, 2.24 mmol) in methanol (15 ml), was added sodium hydroxide (0.134 g, 3.36 mmol) in water (10 ml). The solution was stirred at 5 to 10° C. for 4 hours. The mixture was poured into dichloromethane (40 ml), and washed with cold potassium hydrogen sulphate (3×20 ml), and water (20 ml). The organic layer was dried over sodium sulphate, and evaporated to provide a white foam which was pure enough for the next step.

MS (Fab) m/z 455(MNa$^+$, 100), 377(35), 248(30), 202 (40), 57 (61); $^1$HNMR (CDCl$_3$, 400 MHz) δ (ppm) 8.15–8.30 (2d, 1H, ArH), 7.00–7.70 (m, 3H, COOH, ArH), 5.70–5.76, 5.18–5.23 (m, 1H, NCHCO of indoline), 5.40–5.50, 5.00–5.10 (m, 1H, NH of Abu), 4.65–4.75, 4.20–4.30 (m, 1H, CH of Abu), 3.20–3.70 (m, 2H, CH$_2$ of indoline), 1.60–2.00 (m, 2H, CH$_2$ of Abu), 1.45, 1.42, 1.37 (3s, 9H, t-Bu), 0.90–1.15 (m, 3H, CH$_3$ of Abu).

1-(N-t-Butoxycarbonyl-2(S)-aminobutyryl)-5-trifluoromethoxyindoline-2(R/S)-carboxylic acid (2,2,2-trifluoroethyl)amide 1-(N-t-Butoxycarbonyl-2(S)-aminobutyryl)-5-trifluoromethoxy-indoline-2(S)-carboxylic acid (0.432 g, 1 mmol) and 2,2,2-trifluoroethylamine hydrochloride (0.271 g, 2 mmol) were dissolved in dried dichloromethane (20 ml) under nitrogen at 0° C., and triethylamine (0.7 ml, 5 mmol) was added followed by bis(2-oxo-3-oxazolidinyl) phosphinic chloride (0.509 g, 2 mmol). The temperature was allowed to rise to room temperature and the mixture was stirred at room temperature for 24 hours, then filtered. The filtrate was concentrated under vacuum to give a brown solid which was columned on silica gel using 8:2 dichloromethane: diethyl ether as eluent to provide an off-white solid as the desired product.

MS (Fab) m/z 514(MH$^+$, 25), 458(35), 414(35), 328(65), 202(100), 57(85); $^1$HNMR (CDCl$_3$, 300 MHz) δ (ppm) 8.35–8.45 (m, 1H, CONH), 8.04–8.20, 7.50–7.60 (m, 1H, ArH), 6.90–7.20 (m, 2H, ArH), 4.80–5.55 (m, 2H, NCHCO of indoline, NH of Abu), 3.204.20 (m, 5H, CH$_2$CF$_3$, CH of Abu, CH$_2$ of indoline), 1.55–2.00 (m, 2H, CH$_2$ of Abu), 1.45 (s, 9H, t-Bu), 0.85–1.25 (m, 3H, CH$_3$ of Abu). Elemental analysis: calculated for C$_{21}$H$_{25}$F$_6$N$_3$O$_5$ C, 49.13, H, 4.91, N, 8.18%, found C, 49.20, H, 4.83, N, 8.11%

1-(2(S)-Aminobutyryl)-5-trifluoromethoxyindoline-2(R/S)-carboxylic acid (2,2,2-trifluoroethyl)amide trifluoroacetate 1-(N-t-Butoxycarbonyl-2(S)-aminobutyryl)-5-trifluoromethoxyindoline-2(R/S)-carboxylic acid (2,2,2-trifluoroethyl)amide (260 mg, 0.5 mmol) was dissolved in dichloromethane (2 ml) in an ice-water bath, and trifluoroacetic acid (0.8 ml) was added under nitrogen. The solution was stirred at 0 to 5° C. until gas evolution ceased. The solution was evaporated to dryness in vacuo and the residue was treated with dried diethyl ether. A brown foam was obtained.

MS (Fab) m/z 827(2MH$^+$, 5), 414 (MH$^+$, 100), 328(10), 202(15), 58(50); $^1$HNMR (DMSO-d$_6$, 400 MHz) δ (ppm) 9.20–9.35 (2t, 1H, CONH), 8.30–8.50 (m, 3H, acidic H), 8.19, 8.08 (d, 1H, ArH), 7.20–7.50 (m, 2H, ArH), 5.39–5.42, 5.19–5.23(m, 1H, NCHCO of indoline), 3.50–4.10 (m, 4H, CH$_2$CF$_3$, CH of Abu, one CH$_2$ of indoline), 2.90–3.20 (m, 1H, one CH2 of indoline), 1.70–2.05 (m, 2H, CH$_2$ of Abu), 1.04, 0.98, 0.90 (3t, 3H, CH$_3$ of Abu). IR (KBr) cm$^{-1}$ 3463(broad, w) (N—H, O—H); 1688(vs), 1671(vs) (C=O); 1620(w), 1486(m) (C=C); 1268(vs), 1209(vs), 1171(s) (C—O, C—N, C—F). Elemental Analysis: calculated for C$_{16}$H$_{17}$F$_6$N$_3$O$_3$, 1.9CF$_3$COOH, C, 37.75, H, 3.02, N, 6.67% , found C, 37.97, H, 3.09, N, 6.42%.

EXAMPLE 11

Synthesis of 1-[2-(S)-aminobutyryl]-4,5-dichloro-indoline-2-(R/S)-carboxylic acid butyl amide trifluoroacetate Ethyl 4,5-dichloroindole-2-carboxylate 3,4-Dichlorophenylhydrazine hydrochloride (25 g, 117 mmol) was treated with ethyl pyruvate (25.6 ml, 234 mmol) in ethanol (400 ml) and stirred overnight at room temperature. The reaction mixture was cooled to 0° C. and 200 ml of hexane was added. After filtration, 30 g of a light brown yellow precipitate was obtained, mp=108–113° C. This compound (10 g, 36.3 mmol) was cyclised by refluxing for 4 h in toluene in the presence of anhydrous p-toluenesulfonic acid (10 g, 58 mmol) obtaining 4.5 9 (47%) of a mixture of ethyl 4,5-dichloroindole-2-carboxylate and ethyl 5,6-dichloroindole-2-carboxylate which were separated by flash column chromatography on silica gel using benzene as eluent. MP: 215–217° C.

4,5-Dichloroindoline-2-(R/S)-carboxylic acid methyl ester

This compound was prepared from ethyl 4,5-dichloroindole-2-carboxylate as described in Example 1, using 6–7 eq. of magnesium turnings instead of 2–3 eq. of magnesium turnings.

1-[N-t-Butoxycarbonyl-2-(S)-aminobutyryl]-4,5-dichloroindoline-2-(R/S)-carboxylic acid methyl ester This compound was prepared from 4,5-dichloroindoline-2-(R/S)-carboxylic acid methyl ester as described in Example 1. The product can be used for the next reaction with or without the separation of two diastereoisomers by column chromatography on silica gel.

1-[N-t-Butoxycarbonyl-2-(R/S)-aminobutyryl]-4,5-dichloroindoline-2-(R/S)-carboxylic acid This compound was prepared from 4,5-dichloroindoline-2-(R/S)-carboxylic acid methyl ester as described in Example 1. The product can be used for the next reaction with or without the separation of two diastereoisomers by column chromatography on silica gel.

1-[N-t-Butoxycarbonyl-2-(S)-aminobutyryl]-4,5-dichloroindoline-2-(R/S)-carboxylic acid butyl amide This compound was prepared from 1-(N-t-butoxycarbonyl-2-(S)-aminobutyryl)-4,5-dichloroindoline-2-(R/S)-carboxylic acid as described in Example 1, using butylamine instead of trifluoroethylamine hydrochloride.

1-[2-(S)-Aminobutyryl]-4,5-dichloroindoline-2-(R/S)-carboxylic acid butyl amide trifluoroacetate This compound was prepared from 1-(N-t-butoxycarbonyl-2-(S)-aminobutyryl)-4,5-dichloroindoline-2-(R/S)-carboxylic acid butyl amide as described in Example 1.

MP: 115–124° C.; Element analysis: $C_{17}H_{23}Cl_2N_3O_2$ $(CF_3COOH)1.9$, Found: C, 42.37%, H, 4.30%, N, 6.85%; Calculated: C, 42.21%, H, 4.26%, N, 6.93%.

EXAMPLE 12

Synthesis of 1-[2-(S)-aminobutyryl]-4,5-dichloro-indoline-2-(S)-carboxylic acid 2,2,2-trifluoroethylamide trifluoroacetate 1-[N-t-Butoxycarbonyl-2-(S)-aminobutyryl-4,5-dichloroindoline-2-(S)-carboxylic acid methyl ester This compound was prepared by the procedure described in Example 11. The (S)-isomer was separated by flash column chromatography on silica gel using petroleum ether: ether (7:3) as eluent.

1-N-t-Butoxycarbonyl-2-(S)-aminobutyryl]-4,5-dichloroindoline-2-(S)-carboxylic acid This compound was prepared from 1-(N-t-Butoxycarbonyl-2-(S)-aminobutyryl)-4,5-dichloroindoline-2-(S)-carboxylic acid methyl ester as described in Example 1.

1-[N-t-Butoxycarbonyl-2-(S)-aminobutyryl]4,5-dichloroindoline-2-(S)-carboxylic acid 2,2,2-trifluoroethylamide This compound was prepared from 1-(N-t-butoxycarbonyl-2-(S)-aminobutyryl)-4,5-dichloroindoline-2-(S)-carboxylic acid as described in Example 1.

1-[2-(S)-Aminobutyryl]-4,5-dichloroindoline-2-(S)-carboxylic-acid-2,2,2-trifluoroethylamide trifluoroacetate This compound was prepared from the above compound as described in Example 1.

MP: 92–108° C.; Element analysis: $C_{15}H_{16}C_{12}F_3N_3O_2$ $(CF_3COOH)1.4(CH_3COCH_3)0.2$; Found: C, 38.94%, H, 3.08%, N, 7.32%; Calculated: C, 38.81%, H, 3.29%, N, 7.38%.

EXAMPLE 13

Synthesis of 1-[2-(S)-aminobutyryl]-5,6-dichloro-indoline-2-(S)-carboxylic acid 2,2,2-trifluoroethylamide trifluoroacetate Ethyl 5,6-dichloroindole-2-carboxylate This compound was prepared from 3,4-dichlorophenylhydrazine hydrochloride and ethyl-pyruvate using the procedure described in Example 11.

5,6-Dichloro indoline 2-carboxylic acid methyl ester

This compound was prepared from ethyl 5,6-dichloroindole-2-carboxylate as described in Example 11.

1-[N-Butoxycarbonyl-2-(S)-aminobutyryl]-5,6-dichloroindoline-2-(S)-carboxylic acid methyl ester This compound was prepared from 5,6-dichloroindoline 2-carboxylic acid methyl ester as described in Example 11.

1-[N-t-Butoxycarbonyl-2-(S)-aminobutyryl]-5,6-dichloroindoline-2-(S)-carboxylic acid This compound was prepared from 1-(N-t-butoxycarbonyl-2-(S)-aminobutyryl)-5,6-dichloroindoline-2-(S)-carboxylic acid methyl ester as described in Example 1.

1-[N-t-Butoxycarbonyl-2-(S)-aminobutyryl]-5,6-dichloroindoline-2-(S)-carboxylic acid 2,2,2-trifluoroethylamide This compound was prepared from 1-(N-t-butoxycarbonyl-2-(S)-aminobutyryl)-5,6-dichloroindoline-2-(S)-carboxylic acid as described in Example 1.

1-[2-(S)-Aminobutyryl]-5,6-dichloroindoline-2-(S)-carboxylic-acid-2,2,2-trifluoroethylamide trifluoroacetate This compound was prepared from the above compound as described in Example 1.

MP: 145–158° C.; Element analysis: $C_{15}H_{16}C_{12}F_3N_3O_2$ $(CF_3COOH)1.2$, Found: C, 39.09%, H, 3.29%, N, 7.53%; Calculated: C, 39.06%, H, 3.24%, N, 7.85%.

EXAMPLE 14

Synthesis of 1-[2-(S)-aminobutyryl]-benz-[e]-indoline-2-(S)-carboxylic acid 2,2,2-trifluoroethylamide trifluoroacetate Methyl 2-azido-3-(1-naphthyl) propionate 1-Naphthaldehyde (7 g, 44.87 mmol) and methyl azidoacetate (20.64 g, 179.5 mmol) were dissolved in 210 ml of methanol and cooled to −20° C. Then sodium methoxide (9.66 g, 25% wt.) was added dropwise such that the temperature was kept below −10° C. After stirring at −15° C. for 3 hours, the reaction mixture was kept in refrigerator (4° C.) for 2 days to give the yellow crystalline product which was collected by filtration and washed with cooled hexane to afford pure product as a yellow crystalline solid (8 g, 70%).

Methyl benz[e]indole-2-carboxylate

This compound was prepared from methyl 2-azido-3-(1-naphthyl)propionate as described in Example 7.

Methyl benz[e]indoline-2-carboxylate

This compound was prepared from methyl benz[e] indole-2-carboxylate as described in Example 11.

1-[N-t-Butoxycarbonyl-2-(S)-aminobutyryl]-benz [e]-indoline-2-(S)-carboxylic acid methyl ester This compound was prepared from methyl benz[e] indoline-2-carboxylate as described in Example 1. The (S)-isomer was obtained by recrystallization from a solvent mixture of dichloromethane, ether, hexane as well as methanol.

1-[N-t-Butoxycarbonyl-2-(S)-aminobutyryl]-benz [e]-indoline-2-(S)-carboxylic acid This compound was prepared from 1-(N-t-butoxycarbonyl)-2-(S)-aminobutyryl)-benz[e]-indoline-2-(S)carboxylic acid methyl ester as described in Example 1.

1-[N-t-Butoxycarbonyl-2-(S)-aminobutyryl]-benz [e]-indoline-2-(S)-carboxylic acid 2,2,2-trifluoroethylamide This compound was prepared was prepared from 1-(N-t-butoxycarbonyl)-2-(S)-aminobutyryl)-benz[e]-indoline-2-(S)-carboxylic acid as described in Example 1.

Element analysis: $C_{24}H_{28}F_3N_3O_4$; Found: C, 60.24%, H, 5.79%, N, 8.64%; Calculated: C, 60.12%, H, 5.88%, N, 8.76%; HPLC purity: 99.6%.

1-[2-(S)-Aminobutyryl]-benz[e]-indoline-2-(S)-
carboxylic-acid-2,2,2-trifluoroethylamide
trifluoroacetate This compound was prepared from the above compound as described in Example 1

MP: 64–78° C., Element analysis: $C_{19}H_{20}F_3N_3O_2$ $(CF_3COOH)1.7(CH_3COCH_3)0.5$, Found: C, 47.73%, H, 4.04%, N, 6.81%; Calculated: C, 47.66%, H, 4.13%, N, 6.98%

EXAMPLE 15

Synthesis of 1-[2-(S)-aminobutyryl]-5-O-sulfato-
indoline-2(R/S)-carboxylic acid butyl amide
trifluoroacetate 1-[N-t-Butoxycarbonyl-2(S)-aminobutyryl]-5-
benzyloxyindoline-2(R/S)-carboxylic acid butyl
amide This compound was prepared from 1-(N-t-butoxycarbonyl-2(S)-aminobutyryl)-5-benzyloxyindoline-2-(R/S)-carboxylic acid and butyl amine as described in Example 6.

1-[N-t-Butoxycarbonyl-2(S)-aminobutyryl]-5-
hydroxyindoline-2-(R/S)-carboxylic acid butyl
amide This compound was prepared from 1-(N-t-butoxycarbonyl-2(S)-aminobutyryl)-5-benzyloxyindoline-2-(R/S)-carboxylic acid butyl amide as described in Example 6.

1-[N-t-Butoxycarbonyl-2(S)-aminobutyryl]-5-O-
triethylammonium-sulfate indoline-2-(R/S)-
carboxylic acid butyl amide 1-(N-t-Butoxycarbonyl-2(S)-aminobutyryl)-5-hydroxyindoline-2-(R/S)-carboxylic acid butyl amide (70 mg, 0.17 mmol) was dissolved in the minimum volume of anhydrous pyridine (1.5 ml) required to effect complete solution. To this solution was added solid triethylamine-sulfur trioxide (152 mg, 0.84 mmol). After stirring at 0° C. for 3 hours and room temperature for 2 days, the pyridine was removed by vacuum and the remaining solid was purified by preparative TLC using dichloromethane/methanol as eluent to afford 65 mg of the title product as a white crystalline solid.

MS[ESP](negative)=498 [M–NHEt$_3$](100%).

1-[2(S)-Aminobutyryl]-5-O-sulfato-indoline-2-(R/
S)-carboxylic acid butyl amide trifluoroacetate This compound was prepared from the above compound as described in Example 1, using less excess trifluoroacetic acid and low reaction temperature (−10 to −5° C.).

MP: 85–135° C.; Element analysis: $C_{17}H_{25}N_3O_6S$ $(CF_3COOH)0.4(H_2O)0.4(CH_3OH)0.5$, Found: C, 47.25%, H, 6.31%, N, 9.10%; Calculated: C, 46.94%, H, 6.07%, N, 8.97%; HPLC purity: 99.3% (55.53%+43.8%)(R+S isomer); MS(FAB): 400[M+1](40%), 422[M+Na](16%).

EXAMPLE 16

Synthesis of 1-[2-(S)-aminobutyryl]-benz-[e]-
indoline-2-(S)-carboxylic acid butyl amide
trifluoroacetate 1-[-N-t-Butoxycarbonyl]-2-(S)-aminobutyryl)-benz
[e]-indoline-2-(S)-carboxylic acid butyl amide Was prepared from 1-(N-t-butoxycarbonyl)-2-(S)-aminobutyryl)-benz[e]-indoline-2-(S)-carboxylic acid and butylamine as described in Example 14 and deprotected to give the title product as described in Example 1.

MP: 76–88° C. Element analysis: $C_{21}H_{27}N_3O_2$ $(CF_3COOH)1.5(CH_3COCH_3)0.5$, Found: C, 55.32%, H, 5.46%, N, 7.56% Calculated: C, 55.33%, H, 5.74%, N, 7.59%. MS(FAB): 354(M+1) 100%. HPLC purity: 98.97%.

EXAMPLE 17

Synthesis of 1-[2-(S)-aminobutyryl]-4,5-dichloro-
indoline-2-(R/S)-carboxylic acid 2,2,2-
trifluoroethylamide trifluoroacetate 1-[N-t-Butoxycarbonyl-2-(S)-aminobutyryl]-4,5-
dichloroindoline-2-(R/S)-carboxylic acid 2,2,2-
trifluoroethylamide This compound was prepared from 1-(N-t-butoxycarbonyl-2-(S)-aminobutyryl)-4,5-dichloroindoline-2-(S/R)-carboxylic acid and butylamine as described in Example 1.

1-[2-(S)-Aminobutyryl]-4,5-dichloroindoline-2-(R/
S)-carboxylic-acid-2,2,2-trifluoroethylamide
trifluoroacetate This compound was prepared from the above compound as described in Example 1.

MP: 68–78° C.; Element analysis: $C_{15}H_{16}Cl_2F_3N_3O_2$ $(CF_3COOH)1.5(CH_3COCH_3)0.3$; Found: C, 38.6%, H, 3.62%, N, 7.22%; Calculated: C, 38.7%, H, 3.32%, N, 7.16%. MS(FAB): 398(M+), 32.5%. HPLC: 98.33%.

EXAMPLE 18

Synthesis of 1-[2-(S)-aminobutyryl]-5-O-sulfato-
indoline-2(R/S)-carboxylic acid trifluoroethylamide
trifluoroacetate 1-[N-t-Butoxycarbonyl-2(S)-aminobutyryl]-5-
benzyloxyindoline-2-(R/S)-carboxylic acid
trifluoroethylamide This compound was prepared from 1-(N-t-butoxycarbonyl-2(S)-aminobutyryl)-5-benzyloxyindoline-2-(R/S)-carboxylic acid and trifluoroethylamine as described in Example 15.

1-[N-t-Butoxycarbonyl-2(S)-aminobutyryl]-5-
hydroxyindoline-2-(R/S)-carboxylic acid
trifluoroethylamide This compound was prepared from 1-(N-t-butoxycarbonyl-2(S)-aminobutyryl)-5-benzyloxyindoline-2-(R/S)-carboxylic acid trifluoroethylamide as described in Example 15.

1-[N-t-Butoxycarbonyl-2(S)-aminobutyryl]-5-O-
triethylammonium-sulfate indoline-2-(R/S)-
carboxylic acid trifluoroethylamide This compound was prepared from 1-(N-t-butoxycarbonyl-2(S)-aminobutyryl)-5-hydroxyindoline-2-(R/S)-carboxylic acid trifluoroethylamide as described in Example 15.

MS(EPS-negative): 524(M-NEt$_3$H), 100%.

1-[2(S)-Aminobutyryl]-5-O-sulfato-indoline-2-(R/
S)-carboxylic acid trifluoroethylamide
trifluoroacetate This compound was prepared from the above compound as described in Example 15.

MP: 145–160° C.; Element analysis: $C_{15}H_{18}F_3N_3O_6S$ $(CF_3COOH)0.5(H_2O)0.5(CH_3OH)1.0$, Found: C, 38.96%, H, 4.63%, N, 8.14%; Calculated: C, 39.01%, H, 4.53%, N, 8.03%; HPLC purity: 99.4% (68.35%+31.2%)(R+S isomer); MS(FAB): 426[M+1](100%).

EXAMPLE 19

Synthesis of 1-[2-(S)-aminobutyryl]-benz[f]-indoline-2-(S/R)-carboxylic acid 2,2,2-trifluoroethylamide trifluoroacetate hemi hydrate 2-(Trichloroacetyl)pyrrole This compound was prepared from pyrrole as described in literature (J. Org. Chem. 1993 58, 26, 7246).

Ethyl pyrrole-2-carboxylate

This compound was prepared from 2-(trichloroacetyl) pyrrole as described in literature (J. Org. Chem. 1993, 58, 25, 7246).

2-[(5-Ethoxycarbonypyrrole-3-yl)carbonyl] benzoic acid

This compound was prepared from ethyl pyrrole-2-carboxylate as described in literature (J. Chem. Soc. Perkin Trans I 1988, 3005).

2-[(5-Ethoxycarbonylpyrrol-3-yl)methyl] benzoic Acid

This compound was prepared from 2-[(5-ethoxylcarbonylpyrrole-3-yl)carbonyl] benzoic acid as described in literature (J. Chem. Soc. Perkin Trans I 1988, 3005).

Ethyl 4-{[(2-hydroxymethyl)phenyl]methyl}-1H-pyrrole-2-carboxylate

This compound was prepared from 2-[(5-ethoxycarbonylpyrrole-3-yl) methyl] benzoic acid as described in literature (J. Heterocyclic Chem. 1993, 30, 217).

Ethyl 4-[(2-formylphenyl)methyl]-1H-pyrrole-2-carboxylate

This compound was prepared from Ethyl 4-{[(2-Hydroxymethyl)phenyl]methyl}-1H-pyrrole-2-carboxylate as described in literature (J. Heterocyclic Chem. 1993, 30, 217).

Ethyl benz[f]indole 2-carboxylate

This compound was prepared from ethyl 4-[(2-formylphenyl)methyl]-1H-pyrrole-2-carboxylate as described in literature (J. Heterocyclic Chem. 1993, 30, 217).

Methyl benz[f]indoline 2-carboxylate

This compound was prepared from ethyl benz[f]indole 2-carboxylate as described in Example 1.

1-[N-t-Butoxycarbonyl-2-(S)-aminobutyryl]-benz[f] indoline 2-(S)-carboxylic acid methyl ester This compound was prepared from methyl benz[f] indoline 2-carboxylate as described in Example 1. The (S)-isomer was separated by column chromatography on silica gel.

1-[N-t-Butoxycarbonyl-2-(S)-aminobutyryl]-benz[f] indoline 2-(S)-carboxylic acid This compound was prepared from the above compound as described in Example 1.

1-[N-t-Butoxycarbonyl-2-(S)-aminobutyryl]-benz[f] indoline 2-(S)-carboxylic acid 2,2,2-trifluoroethylamide This compound was prepared from the above compound as described in Example 1.

1-[2-(S)-Aminobutyryl]-benz[f]indoline 2-(S)-carboxylic acid 2,2,2-trifluoroethylamide trifluoroacetate hemi hydrate This compound was prepared from the above compound as described in Example 1.

MP: 102–114° C. Element analysis: $C_{19}H_{20}F_3N_3O_2$ $(CF_3CO_2H)1.2(H_2O)0.5(Et_2O)0.1$, Found: C, 49.34%, H, 4.19%, N, 7.54%, Calculated: C, 49.16%, H, 4.39%, N, 7.89%. HPLC purity: 98.9% MS(FAB): 380(M+1), 64.4%.

EXAMPLE 20

Synthesis of 1-[2-(S)-phenylalanyl]-5-Cl-indoline 2 (R/S)-carboxylic acid 2,2,2-trifluoroethylamide trifluoroacetate 5-Chloro-indoline 2(R/S)-carboxylic acid methyl ester This compound was prepared from ethyl 5-chloro indole carboxylate as described in Example 1.

1-[N-tButoxycarbonyl-2(S) phenylalanyl]-5-Cl indoline 2(R/S) carboxylic acid methyl ester This compound was prepared from 5-chloro-indoline 2(R/S)-carboxylic acid methyl ester and N-t-Boc-phenyl alanine as described in Example 1.

1-[N -tButoxycarbonyl-2(S) phenylalanyl]-5-Cl indoline 2(R/S) carboxylic acid

This compound was prepared from 1-(N-t-butoxycarbonyl-2(S) phenylalanyl)-5-Cl indoline 2-(R/S) carboxylic acid methyl ester as described in Example 1.

1-[N-tButoxycarbonyl-2(S) phenylalanyl]-5-Cl indoline 2(R/S) carboxylic acid 2,2,2 trifluoroamide.

This compound was prepared from 1-(N-t-butoxycarbonyl-2(S) phenylalanyl)-5-Cl indoline 2(R/S) carboxylic acid as described in Example 1.

1-[2-(S)-phenylalanyl]-5-Cl-indoline 2(R/S)-carboxylic acid 2,2,2-trifluoroethylamide trifluoroacetate This compound was prepared from the above compound as described in Example 1.

MP: 71–80° C. Element Analysis: $C_{20}H_{19}ClF_3N_3O_2$ $(CF_3CO_2H)1.7$; Found: C, 45,39%, H, 3.39%, N, 6.66%, Calculated: 45.36%, H, 3.37%, 6.78%. MS(FAB): 426(M+1), 79.8%. HPLC purity: 99.4%.

EXAMPLE 21

Synthesis of 1-[2(S)-aminobutyryl]-4-methoxyindoline-2(S)-carboxylic acid (2,2,2-trifluoroethyl)amide trifluoroacetate 4-Methoxyindoline-2(S)-carboxylic acid methyl ester This compound was prepared from methyl 4-methoxyindole-2-carboxylate as described in example 1.

1-[N-t-Butoxycarbonyl-2(S)-aminobutyryl]-4-methoxyindoline-2(S)-carboxylic acid methyl ester This compound was prepared from 4-methoxyindoline-2(S)-carboxylic acid methyl ester as described for in example 1. However this time the filtrate was washed with water and the aqueous layer extracted with diethyl ether (3×15 ml). The combined organic layers were dried over anhydrous sodium sulphate and concentrated under reduced pressure to afford a colourless oil which was purified by column chromatography on silica gel using 20:1 dichloromethane:diethyl ether as eluent. A white foam was obtained after drying.

1-[N-t-Butoxycarbonyl-2(S)-aminobutyryl]-4-methoxyindoline-2(S)-carboxylic acid This compound was prepared from 1-[N-t-butoxycarbonyl-2(S)-aminobutyryl]-4-methoxyindoline-2(S)-carboxylic acid methyl ester as described in example 1.

1-[N-t-Butoxycarbonyl-2(S)-aminobutyryl]-4-methoxyindoline-2(S)-carboxylic acid (2,2,2-trifluoroethyl)amide This compound was prepared from 1-[N-t-butoxycarbonyl-2(S)-aminobutyryl]-4-methoxyindoline-2(S)-carboxylic acid as described in example 1.

1-[2(S)-Aminobutyryl]-4-methoxyindoline-2(S)-carboxylic acid (2,2,2-trifluoroethyl)amide trifluoroacetate This compound was prepared from 1-[N-t-butoxycarbonyl-2(S)-aminobutyryl]-4-methoxyindoline-2(S)-carboxylic acid (2,2,2-trifluoroethyl)amide as described in example 1.

mp 125–149° C.; Elemental analysis: $C_{16}H_{20}F_3N_3O_3$; 1.4($CF_3CO_2H$); Found: C, 43.51%, H, 4.33%, N, 8.07%; Calculated: C, 43.51%, H, 4.16%, N, 8.10%; HPLC purity: 97.5% (S isomer).

EXAMPLE 22

Synthesis of 1-[2-glycyl]-5-chloroindoline-2(R/S)-carboxylic acid (2,2,2-trifluoroethyl)amide trifluoroacetate

5-Chloroindoline-2(R/S)-carboxylic acid methyl ester

This compound was prepared from ethyl 5-chloroindole-2-carboxylate as described in example 1. However this time 5–6 equivalence of magnesium turnings were used instead of 2–3 eq. of magnesium turnings.

1-[N-t-Butoxycarbonyl-2-glycyl]-5-chloroindoline-2(R/S)-carboxylic acid methyl ester This compound was prepared from 5-chloroindoline-2(R/S)-carboxylic acid methyl ester and N-t-butoxycarbonylaminoacetic acid as described for in example 21. The product was purified by column chromatography on silica gel using 7:3 petroleum spirit:diethyl ether as eluent.

1-[N-t-Butoxycarbonyl-2-glycyl]-5-chloroindoline-2(R/S)-carboxylic acid

This compound was prepared from 1-[N-t-butoxycarbonyl-2-glycyl]-5-chloroindoline-2(R/S)-carboxylic acid methyl ester as described in example 1.

1-[N-t-Butoxycarbonyl-2-glycyl]-5-chloroindoline-2(R/S)-carboxylic acid (2,2,2-trifluoroethyl)amide This compound was prepared from 1-[N-t-butoxycarbonyl-2-glycyl]-5-chloroindoline-2(R/S)-carboxylic acid as described for in example 21.

1-[2-glycyl]-5-chloroindoline-2(R/S)-carboxylic acid (2,2,2-trifluoroethyl)amide trifluoroacetate This compound was prepared from 1-[N-t-butoxycarbonyl-2-glycyl]-5-chloroindoline-2(R/S)-carboxylic acid (2,2,2-trifluoroethyl)amide as described in example 1.

mp 170–176° C.; Elemental analysis: $C_{13}H_{13}ClF_3N_3O_2$; 1.4($CF_3CO_2H$); Found: C, 38.37%, H, 2.77%, N, 8.39%; Calculated: C, 38.31%, H, 2.93%, N, 8.48%; HPLC purity: 98.2%.

EXAMPLE 23

Synthesis of 1-[2(S)-alanyl]-5-chloroindoline-2(R/S)-carboxylic acid (2,2,2-trifluoroethyl)amide hemitrifluoroacetate

5-Chloroindoline-2(R/S)-carboxylic acid methyl ester

This compound was prepared from ethyl 5-chloroindole-2-carboxylate as described in example 22.

1-[N-t-Butoxycarbonyl-2(S)-alanyl]-5-chloroindoline-2(R/S)-carboxylic acid methyl ester This compound was prepared from 5-chloroindoline-2(R/S)-carboxylic acid methyl ester and N-t-butoxycarbonyl-L-alanine as described in example 21.

1-[N-t-Butoxycarbonyl-2(S)-alanyl]-5-chloroindoline-2(R/S)-carboxylic acid

This compound was prepared from 1-[N-t-butoxycarbonyl-2(S)-alanyl]-5-chloroindoline-2(R/S)-carboxylic acid methyl ester as described in example 1.

1-[N-t-Butoxycarbonyl-2(S)-alanyl]-5-chloroindoline-2(R/S)-carboxylic acid (2,2,2-trifluoroethyl)amide This compound was prepared from 1-[N-t-butoxycarbonyl-2(S)-alanyl]-5-chloroindoline-2(R/S)-carboxylic acid as described in example 21.

1-[$^2$(S)-Alanyl]-5-chloroindoline-2(R/S)-carboxylic acid (2,2,2-trifluoroethyl)amide hemitrifluoroacetate This compound was prepared from 1-[N-t-butoxycarbonyl-2(S)-alanyl]-5-chloroindoline-2(R/S)-carboxylic acid (2,2,2-trifluoroethyl)amide as described in example 1.

mp 158–164° C.; Elemental analysis: $C_{14}H_{15}ClF_3N_3O_2$; 0.5($CF_3CO_2H$); Found: C, 44.40%, H, 3.91%, N, 10.23%; Calculated: C, 44.29% H, 3.84% N, 10.33%; HPLC purity: 99.7% (30.4%+69.3%) (R+S isomer).

EXAMPLE 24

Synthesis of 1-[2(S)-norvalyl]-5-chloroindoline-2(R/S)-carboxylic acid (2,2,2-trifluoroethyl)amide trifluoroacetate

1-[N-t-Butoxycarbonyl-2(S)-norvalyl]-5-chloroindoline-2(R/S)-carboxylic acid methyl ester This compound was prepared from 5-chloroindoline-2(R/S)-carboxylic acid methyl ester and N-t- butoxycarbonylaminopropionic acid as described in example 21. The product was purified by column chromatography on silica gel using 8:2 petroleum spirit:diethyl ether as eluent.

1-[N-t-Butoxycarbonyl-2(S)-norvalyl]-5-chloroindoline-2(R/S)-carboxylic acid

This compound was prepared from 1-[N-t-butoxycarbonyl-2(S)-norvalyl]-5-chloroindoline-2(R/S)-carboxylic acid methyl ester as described in example 1.

1-[N-t-Butoxycarbonyl-2(S)-norvalyl]-5-chloroindoline-2(R/S)-carboxylic acid (2,2,2-trifluoroethyl)amide This compound was prepared from 1-[N-t-butoxycarbonyl-2(S)-norvalyl]-5-chloroindoline-2(R/S)-carboxylic acid as described in example 21.

1-[2(S)-Norvalyl]-5-chloroindoline-2(R/S)-carboxylic acid (2,2,2-trifluoroethyl)amide trifluoroacetate This compound was prepared from 1-[N-t-butoxycarbonyl-2(S)-norvalyl]-5-chloroindoline-2(R/S)-carboxylic acid (2,2,2-trifluoroethyl)amide as described in example 1.

mp 130–138° C.; Elemental analysis: $C_{16}H_{19}ClF_3N_3O_2$; 1.4($CF_3CO_2H$); Found: C, 42.07%, H, 3.63%, N, 8.02%; Calculated: C, 42.02%, H, 3.83% N, 7.82%. HPLC purity: 98.3% (R+S isomer)

EXAMPLE 25

Synthesis of 1-[2(S)-methionyl]-5-chloroindoline-2(R/S)-carboxylic acid (2,2,2-trifluoroethyl)amide trifluoroacetate 1-[N-t-Butoxycarbonyl-2(S)-methionyl]-5-chloroindoline-2(R/S)-carboxylic acid methyl ester This compound was prepared from 5-chloroindoline-2(R/S)-carboxylic acid methyl ester and N-t-butoxycarbonyl-L-methionine as described in example 21. The product was purified by column chromatography on silica gel using 3:1 petroleum spirit:ethyl acetate as eluent.

1-[N-t-Butoxycarbonyl-2(S)-methionyl]-5-chloroindoline-2(R/S)-carboxylic acid

This compound was prepared from 1-[N-t-butoxycarbonyl-2(S)-methionyl]-5-chloroindoline-2(R/S)-carboxylic acid methyl ester as described in example 1. The product was purified by column chromatography on silica gel using 5:1 dichloromethane:methanol as eluent.

1-[N-t-Butoxycarbonyl-2(S)-methionyl]-5-chloroindoline-2(R/S)-carboxylic acid (2,2,2-trifluoroethyl)amide This compound was prepared from 1-[N-t-butoxycarbonyl-2(S)-methionyl]-5-chloroindoline-2(R/S)-carboxylic acid as described for in example 21.

1-[2(S)-Methionyl]-5-chloroindoline-2(R/S)-carboxylic acid (2,2,2-trifluoroethyl)amide trifluoroacetate This compound was prepared from 1-[N-t-butoxycarbonyl-2(S)-methionyl]-5-chloroindoline-2(R/S)-carboxylic acid (2,2,2-trifluoroethyl)amide as described in example 1. The product was purified by column chromatography on silica gel using 5:1 dichloromethane: methanol as eluent.

mp 139–145° C.; Elemental analysis: $C_{16}H_{19}ClF_3N_3O_2S$; 0.1($CF_3CO_2H$); Found: C, 46.41% H, 4.62%, N, 10.04%; Calculated: C, 46.19%, H, 4.57%, N, 9.97%; HPLC purity: 98.6% (R+S isomer)

EXAMPLE 26

Synthesis of 1-[2(S)-aminobutyryl]-4-methylindoline-2(R/S)-carboxylic acid (2,2,2-trifluoroethyl)amide trifluoroacetate Ethyl azidoacetate This compound was prepared from ethyl bromoacetate as described in example 7.

Ethyl 2-azido-3-(2-methylphenyl)butanoate

Sodium pieces (5.15 g, 240 mmol) were added in portions to ethanol (157 ml). The resulting solution was cooled in an ice/acetone bath to −15° C. and then over one hour a mixture of 2-methylbenzaldehyde (7.209 g, 60 mmol) and ethyl azidoacetate (30.980 g, 240 mmol) was added at a rate that maintained the temperature below 10° C. After 3 hours, the solution was stored at 5° C. for two days to give pure product as yellow crystals.

4-Methylindole-2-carboxylic acid ethyl ester

This compound was prepared from ethyl 2-azido-3-(2-methylphenyl)butanoate as described in example 7.

4-Methylindoline-2(R/S)-carboxylic acid ethyl ester

This compound was prepared from 4-methylindole-2-carboxylic acid ethyl ester as described in example 7. The product was purified by column chromatography on silica gel using 20:1 dichloromethane: diethyl ether as eluent.

1-[N-t-Butoxycarbonyl-2(S)-aminobutyryl]-4-methylindoline-2(R/S)-carboxylic acid methyl ester This compound was prepared from 4-methylindoline-2(R/S)-carboxylic acid methyl ester as described in example 7.

1-[N -t-Butoxycarbonyl-2(S)-aminobutyryl]-4-methylindoline-2(R/S) carboxylic acid This compound was prepared from 1-[N-t-butoxycarbonyl-2(S)-aminobutyryl]-4-methylindoline-2(R/S)-carboxylic acid methyl ester as described in example 7.

1-[N-t-Butoxycarbonyl-2(S)-aminobutyryl]-4-methylindoline-2(R/S)-carboxylic acid (2,2,2-trifluoroethyl)amide This compound was prepared from 1-[N-t-butoxycarbonyl-2(S)-aminobutyryl]4-methylindoline-2(R/S)-carboxylic acid as described in example 7.

1-[2(S)-Aminobutyryl]-4-methylindoline-2(R/S)-carboxylic acid (2,2,2-trifluoroethyl)amide trifluoroacetate This compound was prepared from 1-[N-t-butoxycarbonyl-2(S)-aminobutyryl]4-methylindoline-2(R/S)-carboxylic acid (2,2,2-trifluoroethyl)amide as described in example 7.

mp 109–122° C.; Elemental analysis: $C_{16}H_{20}F_3N_3O_2$; 1.3($CF_3CO_2H$); Found: C, 45.54%, H, 4.03%, N, 8.83%; Calculated: C, 45.45% H, 4.37%, N, 8.55%; HPLC purity: 98.6% (R+S isomer).

EXAMPLE 27

Synthesis of 1-[2(S)-aminobutyryl]-4,5-dimethoxyindoline-2(R/S)-carboxylic acid (2,2,2-trifluoroethyl)amide trifluoroacetate Methyl 2-azido-3-(2,3-dimethoxyphenyl)propenoate This compound was prepared from 2,3-dimethoxybenzaldehyde as described in example 7.

4,5-Dimethoxyindole-2-carboxylic acid methyl ester

This compound was prepared from methyl 2-azido-3-(2, 3-dimethoxyphenyl)propenoate as described in example 26. The product was purified by column chromatography on silica gel using 4:1 petroleum spirit:ethyl acetate as eluent.

4,5-Dimethoxyindoline-2(R/S)-carboxylic acid methyl ester

This compound was prepared from 4,5-dimethoxyindole-2-carboxylic acid methyl ester as described in example 22. The product was purified by column chromatography on silica gel using 7:3 petroleum spirit:ethyl acetate as eluent.

1-[N-t-Butoxycarbonyl-2(S)-aminobutyryl]-4,5-dimethoxyindoline-2(R/S)-carboxylic acid methyl ester This compound was prepared from 4,5-dimethoxyindoline-2(R/S)-carboxylic acid methyl ester as described in example 7. The product was purified by column chromatography on silica gel using 3:1 petroleum spirit:ethyl acetate as eluent.

1-[N-t-Butoxycarbonyl-2(S)-aminobutyryl]-4,5-dimethoxyindoline-2(R/S) carboxylic acid This compound was prepared from 1-[N-t-butoxycarbonyl-2(S)-aminobutyryl]-4,5-dimethoxyindoline-2(R/S)-carboxylic acid methyl ester as described in example 7.

1-[N-t-Butoxycarbonyl-2(S)-aminobutyryl]-4,5-dimethoxyindoline-2(R/S)-carboxylic acid (2,2,2-trifluoroethyl )amide This compound was prepared from 1-[N-t-butoxycarbonyl-2(S)-aminobutyryl]-4,5-dimethoxyindoline-2(R/S)-carboxylic acid as described in example 7.

1-[2(S)-Aminobutyryl-]4,5-dimethoxyindoline-2(R/S)-carboxylic acid (2,2,2-trifluoroethyl)amide trifluoroacetate This compound was prepared from 1-[N-t-butoxycarbonyl-2(S)-aminobutyryl]-4,5-dimethoxyindoline-2(R/S)-carboxylic acid (2,2,2-trifluoroethyl)amide as described in example 7.

mp 79–87° C.; Elemental analysis: $C_{17}H_{22}F_3N_3O_4$; 1.7 ($CF_3CO_2H$); Found: C, 42.43%, H, 4.27%, N, 6.91%; Calculated: C, 42.01%, H, 4.10%, N, 7.20%; HPLC purity: 100% (R+S isomer).

EXAMPLE 28

Synthesis of 1-[2(S)-aminobutyryl]-4,6-methylenedioxyindoline-2(R/S)-carboxylic acid (2, 2,2-trifluoroethyl)amide trifluoroacetate 2,3-Methylenedioxy benzaldehyde To a mechanically stirred degassed mixture of 2,3-dihydroxy benzaldehyde (7.80 g, 56 mmol) and cesium carbonate (16.20 g, 84 mmol) in acetonitrile (110 ml) was added bromochloromethane (5.46 g, 84 mmol) and the resulting suspension was heated to reflux. After 5 hours the reaction was cooled to room temperature and filtered through celite with ethyl acetate washings. The filtrate was concentrated and directly chromatographed on silica gel using 9:1 hexane:ethyl acetate as eluent.

Methyl 2-azido-3-(2,3-methylenedioxyphenyl) propenoate

A solution of 2,3-methylenedioxy benzaldehyde (15.76 g, 104 mmol) and methylazidoacetate (48.38 g, 419 mmol) in methanol was cooled to −15° C. using an ice/acetone bath. The resulting solution was then treated over one hour with sodium methoxide (96 ml) at a rate that maintained the temperature below −10° C. After 3 hours, the solution was stored at 5° C. for two days to give crystalline material which was filtered off and washed with hexane.

4,5-Methylenedioxyindole-2-carboxylic acid methyl ester

This compound was prepared from methyl 2-azido-3-(2, 3-methylenedioxyphenyl)propenoate as described in example 26. The product was purified by column chromatography on silica gel using 8:1 petroleum spirit:ethyl acetate as eluent.

4,5-Methylenedioxyindoline-2(R/S)-carboxylic acid

This compound was prepared from 4,5-methylenedioxyindole-2-carboxylic acid methyl ester as described in example 1. However this time 10 equivalence of magnesium turnings were used instead of 2–3 eq. of magnesium turnings. The product was purified by column chromatography on silica gel using 7:3 petroleum spirit-:ethyl acetate as eluent.

1-[N-t-Butoxycarbonyl -2(S)-aminobutyryl]-4,5-methylenedioxyindoline-2(R/S)-carboxylic acid methyl ester This compound was prepared from 4,5-methylenedioxyindoline-2(R/S)-carboxylic acid methyl ester as described in example 1. The product was purified by column chromatography on silica gel using 10:1 petroleum spirit:ethyl acetate as eluent.

1-[N-t-Butoxycarbonyl-2(S)-aminobutyryl]-4,5-methylenedioxyindoline-2(R/S)-carboxylic acid This compound was prepared from 1-[N-t-butoxycarbonyl-2(S)-aminobutyryl]-4,5-methylenedioxyindoline-2(R/S)-carboxylic acid methyl ester as described in example 1. The product was purified by column chromatography on silica gel using 5:1 dichloromethane:methanol as eluent.

1-[N-t-Butoxycarbonyl-2(S)-aminobutyryl]-4,5-methylenedioxyindoline-2(R/S)-carboxylic acid (2, 2,2-trifluoroethyl)amide This compound was prepared from 1-[N-t-butoxycarbonyl-2(S)-aminobutyryl]-4,5-methylenedioxy indoline-2(R/S)-carboxylic acid as described in example 7. The product was purified by column chromatography on silica gel using 3:1 petroleum spirit:ethyl acetate as eluent.

1-[2(S)-Aminobutyryl]-4,5-methylenedioxyindoline-2(R/S)-carboxylic acid (2,2,2-trifluoroethyl)amide trifluoroacetate This compound was prepared from 1-[N-t-butoxycarbonyl-2(S)-aminobutyryl]-4,5-methylenedioxy indoline-2(R/S)-carboxylic acid (2,2,2-trifluoroethyl)amide as described in example 7.

mp 89–98° C.; Elemental analysis: $C_{16}H_{18}F_3N_3O_4$; 1.5 ($CF_3CO_2H$); Found: C, 43.95%, H, 4.13%, N, 7.40%; Calculated: C, 43.68%, H, 4.21%, N, 7.04%; HPLC purity: 100% (47.9%, 52.4%) (R+S isomer).

EXAMPLE 29

Synthesis of 1-[2(S)-aminobutyryl]-5-ethynylindoline-2(R/S)-carboxylic acid (2,2,2-trifluoroethyl)amide trifluoroacetate hydrate 1-[N-t-Butoxycarbonyl-2(S)-aminobutyryl]-5-benzyloxyindoline-2(R/S)-carboxylic acid (2,2,2-trifluoroethyl)amide This compound was prepared from 1-[N-t-butoxycarbonyl-2(S)-aminobutyryl]-5-benzyloxyindoline-2(R/S)-carboxylic acid (from example 6) as described in example 1. The product was purified by column chromatography on silica gel using 3:1 petroleum spirit:ethyl acetate as eluent.

1-[N-t-Butoxycarbonyl-2(S)-aminobutyryl]-5-hydroxyindoline-2(R/S)-carboxylic acid (2,2,2-trifluoroethyl)amide 1-[N-t-butoxycarbonyl-2(S)-aminobutyryl]-5-benzyloxyindoline-2(R/S)-carboxylic acid (2,2,2-trifluoroethyl)amide (1.27 g, 5.39 mmol) in ethyl acetate (28 ml) was hydrogenated under an atmosphere of hydrogen in the prescence of palladium on activated carbon at room temperature for 24 hours. The catalyst was filtered through celite with ethyl acetate washing. The filtrate was concentrated and directly chromatographed on silica gel using 2:3 petroleum spirit:ethyl acetate as eluent.

1-[N-t-Butoxycarbonyl-2(S)-aminobutyryl]-5-trifluoromethyl sulfonato indoline-2(R/S)-carboxylic acid (2,2,2-trifluoroethyl)amide 1-[N-t-butoxycarbonyl-2(S)-aminobutyryl]-5-hydroxyindoline-2(R/S)-carboxylic acid (2,2,2-trifluoroethyl)amide (0.87 g, 1.95 mmol) in pyridine (6 ml) was cooled to 0° C. using an ice bath under an atmosphere of nitrogen. Triflic anhydride (0.66 g, 2.34 mmol) was added. After one hour the solution was stored at 5° C. for a day. The reaction mixture was concentrated and the residue purified by column chromatography on silica gel using 5:1 petroleum spirit:ethyl acetate as eluent.

1-[N-t-Butoxycarbonyl-2(S)-aminobutyryl]-5-(trimethylsilyl)ethynyl indoline-2(R/S)-carboxylic acid (2,2,2-trifluoroethyl)amide A mixture of 1-[N-t-butoxycarbonyl-2(S)-aminobutyryl]-5-trifluoromethyl sulfonateindoline-2(R/S)-carboxylic acid (2,2,2-trifluoroethyl)amide (0.83 g, 1.43 mmol), trimethylsilyl acetylene (0.24 ml, 2.15 mmol), triethylamine (2.26 ml) and dichlorobis(triphenylphosphine)palladium (70 mg, 0.10 mmol) in dimethylformamide (11 ml) was stirred at 90° C. for 4 hours under an atmosphere of nitrogen. The reaction mixture was then cooled to room temperature, diluted with brine and extracted with ethyl acetate. The organic layers were dried over anhydrous magnesium sulphate and evaporated in vacuo. The crude residue was purified by column chromatography on silica gel using 4:1 petroleum spirit:ethyl acetate as eluent.

1-[N-t-Butoxycarbonyl-2(S)-aminobutyryl]-5-ethynylindoline-2(R/S)-carboxylic acid (2,2,2-trifluoroethyl)amide To the solution of 1-[N-t-butoxycarbonyl-2(S)-aminobutyryl]-5-(trimethylsilyl)ethynylindoline-2(R/S)-carboxylic acid (2,2,2-trifluoroethyl)amide (0.43 g, 0.81 mmol) in anhydrous methanol (7ml), potassium carbonate (0.02 g) was added under an atmosphere of nitrogen and stirred at room temperature for several hours. The solvent was evaporated in vacuo.

1-[2(S)-Aminobutyryl]-5-ethynylindoline-2(R/S)-carboxylic acid (2,2,2-trifluoroethyl)amide trifluoroacetate hydrate This compound was prepared from 1-[N-t-butoxycarbonyl-2(S)-aminobutyryl]-5-ethynylindoline-2(R/S)-carboxylic acid (2,2,2-trifluoroethyl)amide as described in example 7.

mp 140–149° C.; Elemental analysis: $C_{17}H_{18}F_3N_3O_3$; 2.3($CF_3CO_2H$):1.0($H_2O$); Found: C, 40.87%, H, 3.75%, N, 6.46%; Calculated: C, 40.93%, H, 3.55%, N, 6.63%; HPLC purity: 100% (45.3%, 54.6%) (R+S isomer).

Measurement of the Inhibition of Tripeptidyl Peptidase II (TPP II)

The inhibition of TPP II was measured using the procedure described in WO 96/35805.

The potency of the compounds of the invention was evaluated by measuring the activity of membrane TPP II. The degree of inhibition by the compounds of the invention is expressed as the dissociation constant (Ki), calculated from the concentration needed to provide 50% inhibition, and from the $K_m$ of the substrate (23 $\mu$M).

Membranes of rat cerebral cortex were obtained by centrifugation (200,000×g min) of a homogenate in 10 volumes of a 50 mM potassium phosphate buffer, pH 7.4.

The centrifugation pellet was carefully washed and taken up in a buffer containing 10% glycerol and 0.1% Brij 35 to obtain a concentration of 25 mg protein/ml.

After 25 minutes of preincubation, incubation is carried out in 0.1 ml of a buffer containing 0.1% Brij 35, 100 mM bestatin, 25 $\mu$g of membrane protein and 50 $\mu$m of substrate Ala-Ala-Phe-Amc (AAF-Amc). Liberation of 7-amino4-methylcoumarin (Amc) is evaluated by fluorimetry.

Table 1 shows the inhibition data obtained for the compounds of Examples 1 to 10.

TABLE 1

Inhibition of AAF-Amc Hydrolysis by Cerebral Membranes.

| Compound of Example | Ki (nM) |
| --- | --- |
| 1 | 0.40 |
| 2 | 1.7 |
| 3 | 15 |
| 4 | 3 |
| 5 | 1.2 |
| 6 | 2.8 |
| 7 | 0.56 |
| 8 | 0.36 |
| 9 | 0.7 |
| 10 | 1.1 |

Table 2 shows comparative data between the following comparative compounds known in the art for their inhibiting activity on TPP II and some compounds of the invention:

C.C.1: 1-(2(S)-aminobutyryl)-5-chloroindoline-2(S)-carboxylic acid n-butylamide

C.C.2: 1-(2(S)-aminobutyryl)-indoline-2(S)-carboxylic acid n-butylamide (named Butabindide);

C.C.3: 1-(2(S)-aminobutyryl)-indoline-2(S)carboxylic acid ethylamide

C.C.4: 1-(2(S)-aminobutyryl)-5-hydroxyindoline-2(R/S)-carboxylic acid n-butylamide C.C.5: 1-(2(S)-aminobutyryl)-5-methoxyindoline-2(R/S)-carboxylic acid n-butylamide

TABLE 2

Inhibition of AAF-Amc Hydrolysis by Cerebral Membranes

| Comparative compound | Ki (nM) | Compound of the invention | Ki (nM) |
|---|---|---|---|
| C.C.1 | 2.5 | ex. 1 | 0.4 |
| C.C.2 | 7 | ex. 4 | 3 |
| C.C.3 | 12 | ex. 5 | 1.2 |
| C.C.4 | 6.6 | ex. 6 | 2.8 |
| C.C.5 | 8 | ex. 9 | 0.7 |

What is claimed is:

1. A compound of the following formula I:

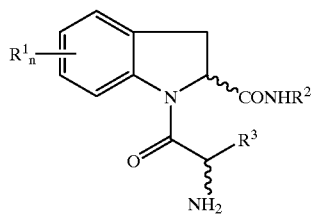

(I)

wherein:
each $R^1$ may be the same or different, and is selected from the group consisting of halogen, OH; $C_1$–$C_6$ alkyl optionally substituted by one or more radicals selected from the group consisting of halogen and OH; ($C_1$–$C_6$) alkenyl optionally substituted by one or more radicals selected from the group consisting of halogen and OH; ($C_1$–$C_6$) alkynyl, optionally substituted by one or more radicals selected from the group consisting of halogen and OH, X($C_1$–$C_6$)alkyl, wherein X is S, O or OCO, and the alkyl is optionally substituted by one or more radicals selected from the group consisting of halogen and OH; $SO_2$($C_1$–$C_6$)alkyl, optionally substituted by at least one halogen, $YSO_3H$, $YSO_2$($C_1$–$C_6$)alkyl, wherein Y is O or NH and the alkyl is optionally substituted by at least one halogen, a diradical —$X^1$—($C_1$–$C_2$)alkylene-$X^1$— wherein $X^1$ is O or S; and a benzene ring fused to the indoline ring;
n is from 0 to 4;
$R^2$ is $CH_2R^4$, wherein $R^4$ is $C_1$–$C_6$ alkyl substituted by one or more radicals selected from the group consisting of halogen and OH; $(CH_2)_pZ(CH_2)_qCH_3$, wherein Z is O or S, p is from 0 to 5 and q is from 0 to 5, provided that p+q is from 0 to 5; ($C_2$–$C_6$) unsaturated alkyl; or ($C_3$–$C_6$) cycloalkyl;
or $R^2$ is ($C_1$–$C_6$)alkyl or O($C_1$–$C_6$)alkyl, each optionally substituted by at least one halogen;
$R^3$ is H; ($C_1$–$C_6$)alkyl optionally substituted by at least one halogen; $(CH_2)_pZR^5$ wherein p is from 1 to 3, Z is O or S and $R^5$ is H or ($C_1$–$C_3$)alkyl; benzyl; or a pharmaceutically acceptable acid addition salt thereof; provided that:
when $R^1$ is a halogen atom; a O—($C_1$–$C_4$)alkyl; OH or (C1–C4)alkyl group; $R^2$ is $CH_2R^4$ wherein $R^4$ is $(CH_2)_2SCH_3$, —$(CH_2)_2OH$ or cyclohexyl; or $R^2$ is a ($C_1$–$C_6$)alkyl group; then $R^3$ is neither a hydrogen atom nor a ($C_1$–$C_4$)alkyl group.

2. A compound according to claim 1, wherein: each $R^1$ may be the same or different, and is selected from the group consisting of
halogen, OH, ($C_1$–$C_6$)alkyl, optionally substituted by one or more radicals selected from the group consisting of halogen and OH, X($C_1$–$C_6$)alkyl, wherein X is S, O or OCO, optionally substituted by one or more radicals selected from the group consisting of halogen and OH, $SO_2$($C_1$–$C_6$)alkyl, optionally substituted by at least one halogen, $YSO_3H$, and $YSO_2$($C_1$–$C_6$)alkyl, wherein Y is O or NH optionally substituted by at least one halogen;
n is from 0 to 4;
$R^2$ is $CH_2R^4$, wherein $R^4$ is
($C_1$–$C_6$)alkyl substituted by one or more radicals selected from the group consisting of halogen and OH; $(CH_2)_pZ(CH_2)_qCH_3$, wherein Z is O, S, p is from 0 to 5 and q is from 0 to 5, provided that p+q is from 0 to 5; ($C_2$–$C_6$) unsaturated alkyl; or ($C_3$–$C_6$) cycloalkyl; or
$R^2$ is ($C_1$–$C_6$)alkyl or O($C_1$–$C_6$)alkyl, each optionally substituted by at least one halogen;
$R^3$ is H; ($C_1$–$C_6$)alkyl.

3. A compound according to claim 1 wherein $R^3$ is hydrogen, methyl or ethyl.

4. A compound according to claim 1, wherein $R^3$ is a ($C_1$–$C_6$)alkyl optionally substituted by at least one halogen; $(CH_2)_pZR^5$ where p, Z and $R^5$ are as defined in claim 1; or benzyl.

5. A compound according to claim 4, wherein $R^3$ is —$(CH_2)_2SCH_3$.

6. A compound according to claim 1, wherein $R^2$ is $CH_2R^4$, $R^4$ being ($C_1$–$C_6$)alkyl substituted by at least one halogen; $(CH_2)_pZ(CH_2)_qCH_3$ wherein Z is O, p and q are as defined in claim 1; ($C_2$–$C_6$) unsaturated alkyl; or $R^2$ is O ($C_1$–$C_6$)alkyl optionally substituted by at least one halogen.

7. A compound according to claim 1, wherein $R^2$ is $CH_2R^4$, $R^4$ is selected from the group consisting of $CH_2OCH_3$, $CH_2SCH_3$, $SCH_3$, $CH(OH)CH_3$, C=$CH_2$, C≡CH and cyclopropyl; or $R^2$ is $NHCH_3$.

8. A compound according to claim 1, wherein $R^2$ contains at least one halogen atom.

9. A compound according to claim 8, wherein $R^2$ is $CH_2R^4$ with $R^4$ selected from the group consisting of $CHF_2$, $CF_3$, $CF_2CF_3$, $CH_2F$, and $CH_2Cl$.

10. A compound according to claim 1, wherein n is 0.

11. A compound according to claim 1, wherein n is not 0 and $R^1$ is ($C_1$–$C_6$)alkyl substituted by one or more radicals selected from the group consisting of halogen and OH; X($C_1$–$C_6$)alkyl wherein X is S or OCO, optionally substituted by one or more radicals selected from the group consisting of halogen and OH; O($C_1$–$C_6$)alkyl substituted by one or more radicals selected from the group consisting of halogen and OH; $SO_2$($C_1$–$C_6$)alkyl, optionally substituted by at least one halogen; or $YSO_3H$; $YSO_2$($C_1$–$C_6$)alkyl wherein Y is O or NH optionally substituted by at least one halogen.

12. A compound according to claim 1, wherein $R^1$ is $CH_3$, $OCH_3$, Cl, F, OH, $OCF_3$, $OSO_3H$, $OSO_2CH_3$, $OCOCH_3$, $OSO_2CF_3$, $SO_2CH_3$, $SCH_3$, $NHSO_2CH_3$ or $CF_3$.

13. A compound according to claim 1, wherein n is not 0 and $R^1$ is ($C_1$–$C_6$)alkenyl or ($C_1$–$C_6$)alkynyl.

14. A compound according to claim 13, wherein $R^1$ is —C≡CH—.

15. A compound according to claim 1, wherein n is 1 and $R^1$ is a diradical —$X^1$—($C_1$-$C_2$)alkylene-$X^1$— where $X^1$ is as defined in claim 1.

16. A compound according to claim 15, wherein $R^1$ is —$OCH_2O$—.

17. A compound according to claim 1, wherein n is 1 and $R^1$ is a benzene ring fused to an indoline ring.

18. A compound according to claim 1, wherein n is 1 or 2.

19. A compound according to claim 1, which is selected from the group consisting of:
- 1-(2(S)-aminobutyryl)-5-chloroindoline-2(S)-carboxylic acid (2,2,2-trifluoroethyl)amide,
- 1-(2(S)-aminobutyryl)-5-chloroindoline-2(S)-carboxylic acid 2-chloroethylamide,
- 1-(2(S)-aminobutyryl)-indoline-2(S) carboxylic acid (2-methylthioethyl)amide,
- 1-(2(S)-aminobutyryl)-indoline-2(S)-carboxylic acid N-(cyclopropylmethyl)amide,
- 1-(2(S)-aminobutyryl)-indoline-2(S)-carboxylic acid (2,2,2-trifluoroethyl)amide,
- 1-(2(S)-aminobutyryl)-5-hydroxyindoline-2(R/S)-carboxylic acid (2,2,2-trifluoroethyl)amide,
- 1-(2(S)-aminobutyryl)-4-chloroindoline-2(R/S)-carboxylic acid (2,2,2-trifluoroethyl)amide,
- 1-(2(S)-aminobutyryl)-4-fluoroindoline-2(R/S)-carboxylic acid (2,2,2-trifluoroethyl)amide,
- 1-(2(S)-aminobutyryl)-5-methoxyindoline-2(R/S)-carboxylic acid (2,2,2-trifluoroethyl)amide,
- 1-(2(S)-aminobutyryl)-5-trifluoromethoxyindoline-2(R/S)-carboxylic acid (2,2,2-trifluoroethyl)amide and pharmaceutically acceptable salts thereof.

20. A compound according to claim 1, which is selected from the group consisting of:
- 1-[2-(S)-aminobutyryl]-4,5-dichloro-indoline-2-(R/S)-carboxylic acid butyl amide trifluoroacetate,
- 1-[2-(S)-aminobutyryl]-4,5-dichloro-indoline-2-(S)-carboxylic acid 2,2,2-trifluoroethylamide trifluoroacetate,
- 1-[2-(S)-aminobutyryl]-5,6-dichloro-indoline-2-(S)-carboxylic acid 2,2,2-trifluoroethylamide trifluoroacetate,
- 1-[2-(S)-aminobutyryl]-benz-[e]-indoline-2-(S)-carboxylic acid 2,2,2-trifluoroethylamide trifluoroacetate,
- 1-[2-(S)-aminobutyryl]-5-O-sulfato-indoline-2-(R/S)-carboxylic acid butyl amide trifluoroacetate,
- 1-[2-(S)-aminobutyryl]-benz-[e]-indoline-2-(S)-carboxylic acid butyl amide trifluoroacetate,
- 1-[2-(S)-aminobutyryl]-4,5-dichloro-indoline-2-(R/S)-carboxylic acid 2,2,2-trifluoroethylamide trifluoroacetate,
- 1-[2-(S)-aminobutyryl]-5-O-sulfato-indoline-2-(R/S)-carboxylic acid trifluoroethylamide trifluoroacetate,
- 1-[2-(S)-aminobutyryl]-benz[f]-indoline-2-(S/R)-carboxylic acid 2,2,2-trifluoroethylamide trifluoroacetate hemi hydrate,
- 1-[2-(S)-phenylalanyl]-5-Cl-indoline 2(R/S)-carboxylic acid 2,2,2-trifluoroethylamide trifluoroacetate,
- 1-[2(S)-aminobutyryl]-4-methoxyindoline-2(S)-carboxylic acid (2,2,2-trifluoroethyl)amide trifluoroacetate,
- 1-[2-glycyl]-5-chloroindoline-2(R/S)-carboxylic acid (2,2,2-trifluoroethyl)amide trifluoroacetate,
- 1-[2(S)-alanyl]-5-chloroindoline-2(R/S)-carboxylic acid (2,2,2-trifluoroethyl)amide hemitrifluoroacetate,
- 1-[2(S)-norvalyl]-5-chloroindoline-2(R/S)-carboxylic acid (2,2,2-trifluoroethyl)amide trifluoroacetate,
- 1-[2(S)-methionyl]-5-chloroindoline-2(R/S)-carboxylic acid (2,2,2-trifluoroethyl)amide trifluoroacetate,
- 1-[2(S)-aminobutyryl]-4-methylindoline-2(R/S)-carboxylic acid (2,2,2-trifluoroethyl)amide trifluoroacetate,
- 1-[2(S)-aminobutyryl]-4,5-dimethoxyindoline-2(R/S)-carboxylic acid (2,2,2-trifluoroethyl)amide trifluoroacetate,
- 1-[2(S)-aminobutyryl]-4,5-methylenedioxyindoline-2(R/S)-carboxylic acid (2,2,2-trifluoroethyl)amide trifluoroacetate,
- 1-[2(S)-aminobutyryl]-5-ethynylindoline-2(R/S)-carboxylic acid (2,2,2-trifluoroethyl)amide trifluoroacetate hydrate and pharmaceutically acceptable salts thereof.

21. A process for preparing a compound of formula I according to claim 1, which process comprises a) reacting a compound of the following formula II:

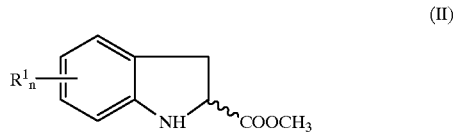

(II)

with an optionally protected amino acid $R^3CH(NHR^{10})COOH$ (III), where n, $R^1$ and $R^3$ are as defined in claim 1 and $R^{10}$ is H or a protecting group, to obtain a compound of the following formula IV:

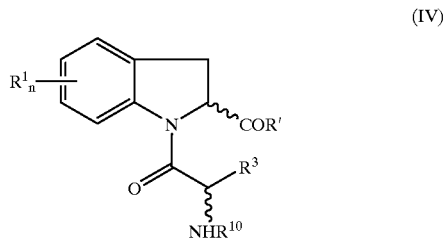

(IV)

wherein $R^1$ is methoxy, b) optionally hydrolysing the ester (IV) to the corresponding acid, c) reacting the acid or ester (IV) with an amine of formula $R^2NH_2$, and d) optionally removing the protecting group $R^{10}$, and optionally converting the product thus obtained into a salt.

22. A process for preparing the compound of formula I according to claim 1, which process comprises
e) reacting a compound of formula V:

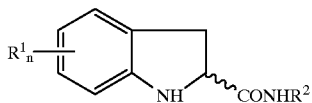

with an optionally protected amino acid of the formula (III) $R^3CH(NHR^{10})COOH$, wherein, n, $R^1$, $R^2$, $R^3$ and $R^{10}$ are as defined in claim 1, to obtain a compound of the following formula (IV):

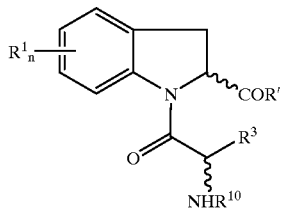

wherein $R^1$ is $NHR^2$, optionally removing the protecting group $R^{10}$, and optionally converting the product thus obtained into a salt.

23. A pharmaceutical composition acting as an inhibitor of the CCK-inactivating peptidase tripeptidyl peptidase (TPP II), which comprises a therapeutically effective amount of a compound according to claim 1, and a pharmaceutically acceptable carrier or diluent.

24. A pharmaceutical composition according to claim 23, further comprising a compound effective in the treatment of obesity, a compound acting on the amylin receptor or a compound that increases the levels of noradrenaline, dopamine or serotonin in the brain.

25. A pharmaceutical composition according to claim 23, comprising an effective dosage of a compound according to claim 1 suitable for an administration of 0.001 to 10 mg per kg body weight per day.

26. A cosmetic composition comprising a compound according to claim 1 and a physiologically acceptable carrier or diluent.

27. Method for the treatment of diseases requiring the inhibition of CCK-inactivating peptidase tripeptidyl peptidase (TPP II) comprising the administration of a therapeutically effective amount of a compound of formula I according to claim 1 to a human in need thereof.

28. Method for the treatment of an over-eating disorder comprising the administration of a therapeutically effective amount of a compound of formula I according to claim 1 to a human in need thereof.

29. Method for the treatment of obesity comprising the administration of a therapeutically effective amount of a compound of formula I according to claim 1 to a human in need thereof.

30. Method according to claim 29 comprising the combined administration of a compound of formula I and of a compound effective in the treatment of obesity.

31. Method according to claim 29 comprising the combined administration of a compound of formula I and of a compound effective in the treatment of obesity selected from the group consisting of an adrenergic $\beta_3$-receptor agonist, a histamine $H_3$-receptor antagonist, a neuropeptide Y receptor (NPY-5)antagonist, a compound acting on an amylin receptor and a compound that increases the levels of noradrenaline, dopamine or serotonin in a brain.

32. Method according to claim 31 comprising the combined administration of a compound of formula I and of a compound selected from the group consisting of dexfenfluramine, sibutramine and fluoxetine.

33. Method for the treatment of psychotic syndromes and associated psychiatric disorders comprising the administration of a therapeutically effective amount of a compound of formula I according to claim 1 to a human in need thereof.

34. Method for slimming comprising the administration of a therapeutically effective amount of a compound of formula I according to claim 1 to a human in need thereof.

35. A pharmaceutical composition according to claim 24 wherein the compound effective in the treatment of obesity is selected from the group consisting of an adrenergic $\beta_3$-receptor agonist, a histamine $H_3$-receptor antagonist, and a neuropeptide Y receptor (NPY-5) antagonist.

36. A pharmaceutical composition according to claim 24 wherein the compound that increases the levels noradrenaline, dopamine or serotonin in the brain is selected from consisting of dexfenfluramine, sibutramine and fluoxetine.

* * * * *

UNITED STATES PATENT AND TRADEMARK OFFICE
CERTIFICATE OF CORRECTION

PATENT NO.   : 6,335,360 B1  
DATED        : January 1, 2002  
INVENTOR(S)  : Schwartz et al.

It is certified that error appears in the above-identified patent and that said Letters Patent is hereby corrected as shown below:

<u>Title page,</u>  
Item [75], please correct to read as follows:  
-- [75] Inventors: Jean-Charles Schwartz, Paris; Christian Rose, Le Mesnil St. Denis, both of (FR); Froylan Vargas, Orangeburg, NY (US); Charon Robin Ganellin, Herts (GB); Lithua Zhao, Lanarkshire (GB); Samad Sanjeeda; Yondjun Chen, both of London (GB) --

Signed and Sealed this

Fourth Day of June, 2002

*Attest:*

JAMES E. ROGAN  
*Attesting Officer*   *Director of the United States Patent and Trademark Office*

UNITED STATES PATENT AND TRADEMARK OFFICE
CERTIFICATE OF CORRECTION

PATENT NO.      : 6,335,360 B1
DATED           : January 1, 2002
INVENTOR(S)     : Schwartz et al.

It is certified that error appears in the above-identified patent and that said Letters Patent is hereby corrected as shown below:

<u>Title page,</u>
Item [75], should read as follows:

-- [75] Inventors: Jean-Charles Schwartz, Paris; Christiane Rose, Le Mesnil St. Denis, both of (FR); Froylan Vargas, Orangeburg, NY (US); Charon Robin Ganellin, Hertz (GB); Lihua Zhao, Glasgow (GB); Sanjeeda Samad, London (GB); Yong jun Chen, Beijing (CH) --

Signed and Sealed this

Sixth Day of May, 2003

JAMES E. ROGAN
*Director of the United States Patent and Trademark Office*